(12) United States Patent
Zerangue

(10) Patent No.: US 7,452,680 B2
(45) Date of Patent: Nov. 18, 2008

(54) MCT1 TRANSPORTERS EXPRESSED IN BLOOD BRAIN BARRIER CELLS

(75) Inventor: Noa Zerangue, Sunnyvale, CA (US)

(73) Assignee: XenoPort, Inc., Santa Clara, CA (US)

( * ) Notice: Subject to any disclaimer, the term of this patent is extended or adjusted under 35 U.S.C. 154(b) by 484 days.

(21) Appl. No.: 11/026,545

(22) Filed: Dec. 30, 2004

(65) Prior Publication Data

US 2005/0170390 A1 Aug. 4, 2005

Related U.S. Application Data

(60) Provisional application No. 60/540,868, filed on Jan. 30, 2004.

(51) Int. Cl.
G01N 33/53 (2006.01)
C07K 14/00 (2006.01)
C07H 21/04 (2006.01)

(52) U.S. Cl. .......................... 435/7.1; 435/7.2; 435/7.3; 435/69.1; 435/235.1; 435/320.1; 435/325; 530/350; 536/23.1; 536/23.5

(58) Field of Classification Search ........................ None
See application file for complete search history.

(56) References Cited

U.S. PATENT DOCUMENTS

| | | |
|---|---|---|
| 6,489,302 B1 | 12/2002 | Wiessler et al. |
| 2003/0158254 A1 | 8/2003 | Zerangue et al. |
| 2004/0072746 A1 | 4/2004 | Sullivan et al. |
| 2005/0032135 A1 | 2/2005 | Zerangue et al. |

FOREIGN PATENT DOCUMENTS

| | | |
|---|---|---|
| WO | WO 01/020331 | 3/2001 |
| WO | WO 03/065982 | 8/2003 |
| WO | WO 2004/033655 | 4/2004 |

OTHER PUBLICATIONS

Alderman, D.A.; "A Review of Cellulose Ethers in Hydrophilic Matrices for Oral Controlled-Release Dosage Forms"; *Int. J. Pharm. Tech. & Prod. Mfr.* 5(3):1-9 (1984).
Altschul, S. et al.; "Basic Local Alignment Search Tool"; *J. Mol. Biol.* 215:403-410 (1990).
Audus, K. et al.; Characterization of an in vitro blood-brain barrier model system for studying drug transport and metabolism, *Pharmaceutical Res.* 3(2):81-87 (1986)).
Audus, K. et al.; The use of cultured epithelial and endothelial cells for drug transport and metabolism studies, *Pharmaceutical Res.* 7(5):435-451 (1990)).
Bamba, M. et al.; "Release Mechanisms in Gelforming Sustained Release Preparations"; *Int. J. Pharmaceuticals* 2:307-315 (1979).
Bowman, P. et al.; "Brain microvessel endothelial cells in tissue culture: A model for study of blood-brain barrier permeability"; *Ann. Neurol.* 14:396-402 (1983).
Brightman and Neuwelt (ed.); Implications of the blood-brain barrier and its manipulation; vol. 1, Plenum Medical, New York, pp. 53-83 (1989).

Cserr, H. et al.,; "Blood-brain interfaces in vertebrates: a comparative approach"; *Am. J. Physiol.—Regulatory, Integrative and Comparative Physiology* 246:277-288 (1984).
During, M. et al.; "Controlled Release of Dopamine from a Polymeric Brain Implant: In Vivo Characterization"; *Ann. Neurol.* 25:351-356 (1989).
Goldstein, G. et al.; "The Blood-Brain Barrier"; *Scientific American* 255(3):74-83 (1986).
Hanes, J. et al.; "New Advances in Microsphere-Based Single-Dose Vaccines"; *Advanced Drug Delivery Reviews* 28:97-119 (1997).
Henikoff, S. et al.; Amino Acid Substitution Matrices from Protein Blocks; *Proc. Natl. Acad. Sci. USA* 89:10915-19 (1989).
Howard, M. et al.; "Intracerebral Drug Delivery in Rats with Lesion-Induced Memory Deficits"; *J. Neurosurg.* 71:105-112 (1898_).
Karlin, S. et al.; "Applications and Statistics for Multiple High-Scoring Segments in Molecular Sequences"; *Proc. Nat'l. Acad. Sci. USA* 90:5873-87 (1993).
Langer, R.; "New Methods of Drug Delivery"; *Science* 249:1527-1533 (1990).
Langer, R. et al.; "Chemical and Physical Structure of Polymers as Carriers for Controlled Release of Bioactive Agents: A Review"; *J. Macromol. Sci. Rev. Macromol Chem.* 23:61-126 (1983).
Levy, R. et al.; "Inhibition of Calcification of Bioprosthetic Heart Valves by Local Controlled-Release Diphosphonate"; *Science* 228:190-192 (1985).
Masereeuw, R. et al.; "In vitro and in vivo transport of zidovudine (AZT) across the blood-brain barrier and the effect of transport inhibitors"; *Pharm. Res.* 11(2):324-330 (1994).
Meresse, S. et al.; "Bovine brain endothelial cells express tight junctions and monoamine oxidase activity in long-term culture"; *J. Neuorchem.* 53:1363-1371 (1989).
Needleman, S. et al.; "A General Method Applicable to the Search for Similarities in the Amino Acid Sequence of Two Proteins"; *J. Mol. Biol.* 48:443-453 (1970).
Pardridge, W. M.; "Receptor-Mediated Peptide Transport Through the Blood-Brain Barrier"; (1986) *Endocrine Rev.* 7(3):314-330 (1986).
Pardridge, W. M. et al.; "Comparison of in vitro and in vivo models of drug transcytosis through the blood-brain barrier"; *J. Pharmacol. Exp. Thera.* 253(2):884-891 (1990).

(Continued)

*Primary Examiner*—Gary B. Nickol
*Assistant Examiner*—Nirmal S Basi
(74) *Attorney, Agent, or Firm*—Townsend and Townsend and Crew LLP

(57) ABSTRACT

MCT1 is consistently expressed at high levels in brain microvessel endothelial cells. Disclosed herein are assays for determining whether a test material/molecule is a substrate for, and/or is actively transported by, the MCT1 transporter, and therefore a candidate substrate for crossing the blood brain barrier. The assays are useful in screening for therapeutic, cytotoxic or imaging compounds used in the treatment or diagnosis of neurological diseases.

17 Claims, 14 Drawing Sheets

OTHER PUBLICATIONS

Pearson, W. et al.; "Improved Tools for Biological Sequence Comparison"; *Proc. Nat'l. Acad. Sci. USA* 85:2444-48 (1988).

Smith, T. et al.; "Comparison of Biosequences"; *Adv. Appl. Math.* 2:482-489 (1981).

Terasaki, T. et al.; "New Approaches to in vitro Models of Blood-Brain Barrier Drug Transport"; *Drug Discovery Today* 8:944-954 (2003).

Froberg et al., "Expression of monocarboxylate transporter MCT1 in normal and neoplastic human CNS tissues," *Neuroreport*, 12(4):761-765 (2001).

Gerhart et al., "Expression of monocarboxylate transporter MCT1 by brain endothelium and glia in adult and suckling rats," *American J. Physiology*, 273(1,pt. 1):E207-E213 (1997).

Shen et al., "Evaluation of an immortalized retinal endothelial cell line as an in vitro model for drug transport studies across the blood-retinal barrier," *Pharmaceutical Research*, 20(9):1357-1363 (2003).

Smith et al., "Regulation of MCT1 Function by Protein Kinase—A and C Pathways in Cerebral Endothelial Cells," *Society fo Neuroscience Abstract Viewer and Itinerary Planner*, abstract No. 581.15 (2002) from 32nd annual meeting of the society for neuroscience, Orlando, Florida Nov. 2-7, 2002.

Tamai et al., "Transporter-mediated permeation of drugs across the blood-brain barrier," *J. Pharmaceutical Sciences*, 89(11):1371-1388 (2000).

Terasaki et al., "Conditionally immortalized cell lines as a new in vitro model for the study of barrier functions," *Biological and Pharmaceutical Bulletin*, 24(2):111-118 (2001).

Figure 1
MCT1 SUBSTRATES
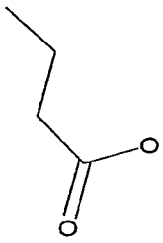
Butyric Acid
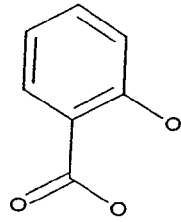
Salicylic Acid
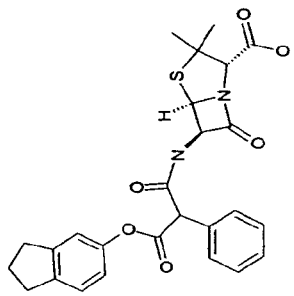
Carindicillin
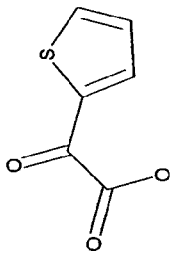
2-Thiophene glyoxylate (thiophenegylyoxylic acid)
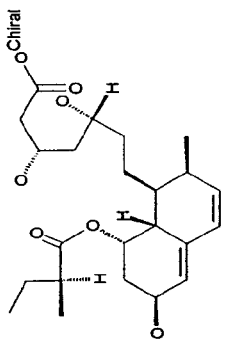
Pravastatin
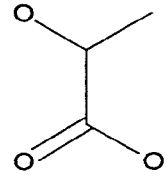
Lactic Acid
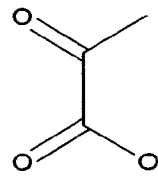
Pyruvic Acid
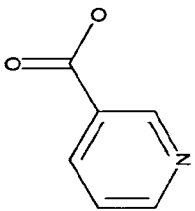
Nicotinic Acid A.
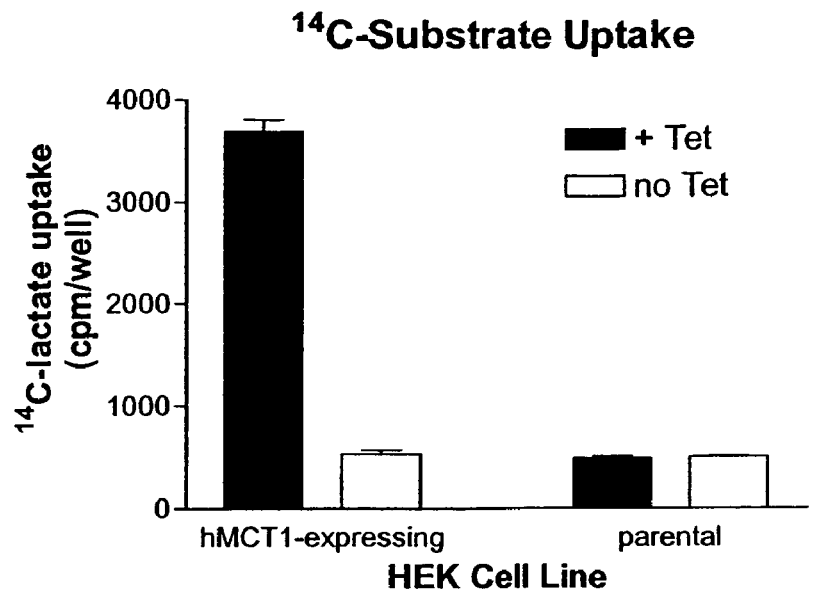
B.
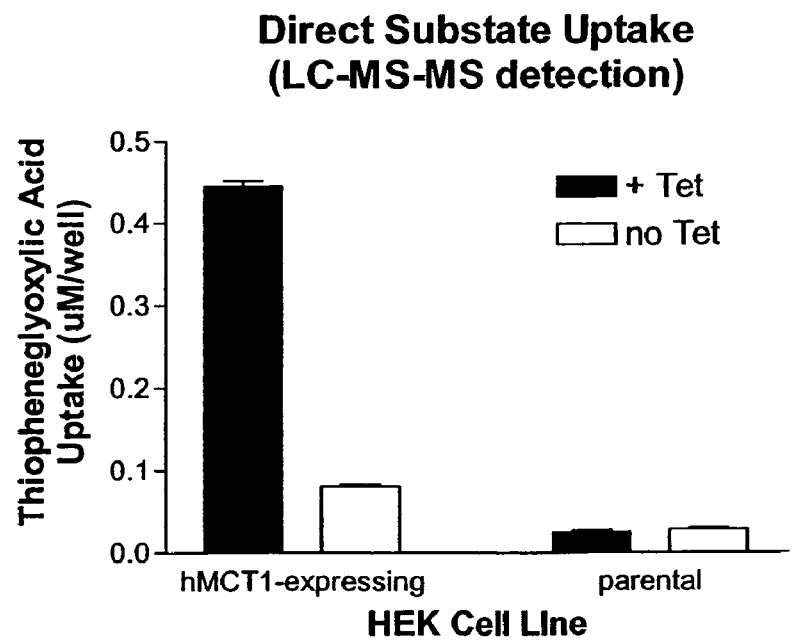
Figure 10

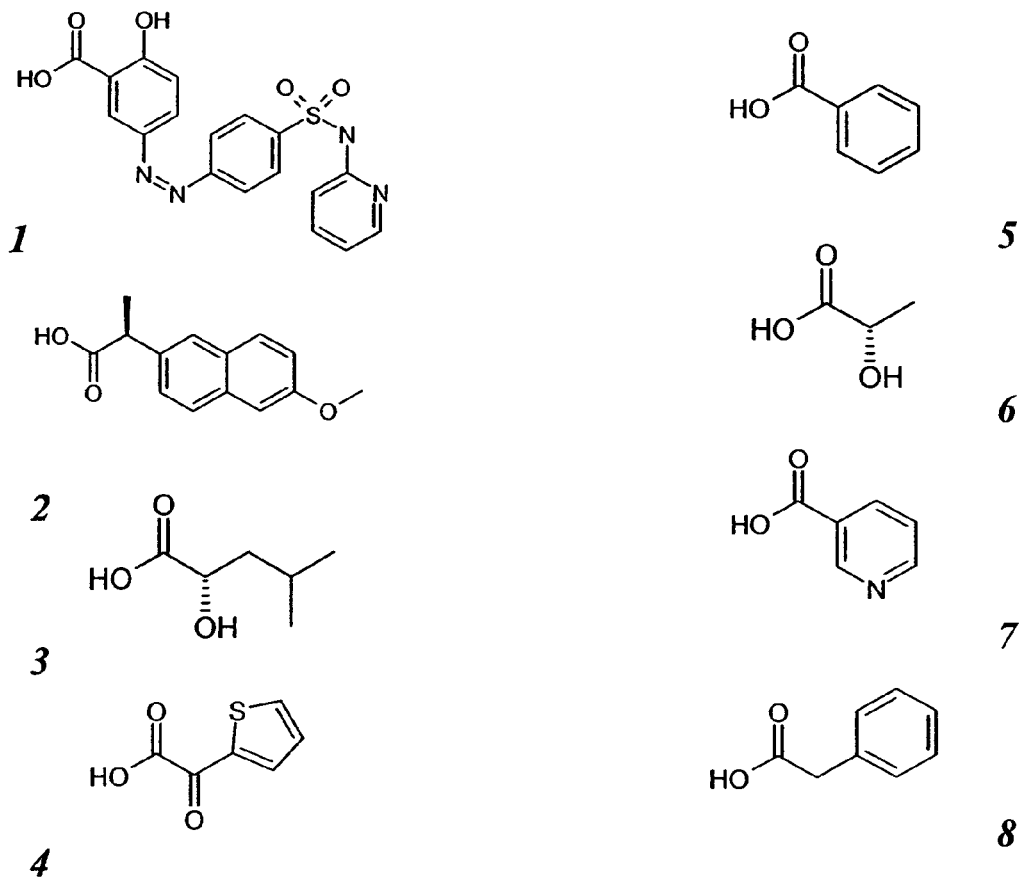
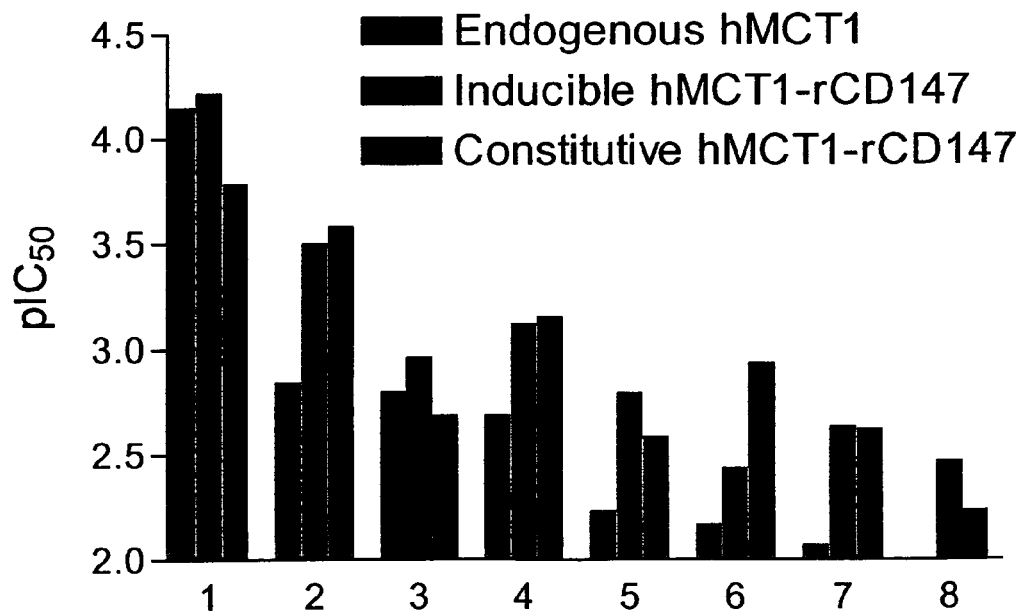
Fig. 13

US 7,452,680 B2

MCT1 TRANSPORTERS EXPRESSED IN BLOOD BRAIN BARRIER CELLS

CONTINUITY

This application claims the benefit of U.S. Provisional Application No. 60/540,868, filed Jan. 30, 2004, the disclosure of which is incorporated by reference herein in its entirety.

TECHNICAL FIELD

The disclosures herein relate to assays and methods of using the same for screening compounds and/or chemical moieties for their ability to be actively transported across the blood brain barrier.

BACKGROUND

The capillaries that supply blood to the tissues of the brain constitute the blood brain barrier (Goldstein et al. (1986) Scientific American 255:74-83; Pardridge, W. M. (1986) Endocrin. Rev. 7:314-330). The endothelial cells which form the brain capillaries are different from those found in other tissues in the body. Brain capillary endothelial cells are joined together by tight intercellular junctions which form a continuous wall against the passive diffusion of molecules from the blood to the brain and other parts of the central nervous system (CNS). These cells are also different in that they have few pinocytic vesicles which in other tissues allow somewhat unselective transport across the capillary wall. Also lacking are continuous gaps or channels running between the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al., cited supra). If the brain was not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated proteins which selectively bind and certain molecules across the barrier membranes. These transporter proteins are known as solute carrier transporters.

The problem posed by the blood-brain barrier is that, in the process of protecting the brain, it excludes many potentially useful therapeutic agents. Presently, only substances which are sufficiently lipophilic can penetrate the blood-brain barrier (Goldstein et al., cited supra; Pardridge, W. M., cited supra). Some drugs can be modified to make them more lipophilic and thereby increase their ability to cross the blood brain barrier. However, each modification must be tested individually on each drug and the modification can alter the activity of the drug.

Because the blood brain barrier is composed of brain microvessel endothelial cells, these cells have been isolated and cultured for use in in vitro model systems for studying the blood brain barrier (Bowman et. al, Brain microvessel endothelial cells in tissue culture: A model for study of blood-brain barrier permeability, Ann. Neurol. 14, 396-402 (1983); Audus and Borchardt, Characterization of an in vitro blood-brain barrier model system for studying drug transport and metabolism, Pharm, Res. 3, 81-87 (1986)). In vitro model systems of the blood brain barrier have been successfully derived from bovine, canine, human, murine, porcine, and rat cells, and have similar permeability properties due to similarity of the physiological characteristics of the blood brain barrier among mammals (Cserr et al., Blood-brain interfaces in vertebrates: a comparative approach, Am. J. Physiol. 246, R277-R288 (1984); Audus et al., The use of cultured epithelial and endothelial cells for drug transport and metabolism studies, Pharm. Res. 7, 435-451 (1990)). In these models, the cultured endothelial cells retain the characteristics of brain endothelial cells in vivo, such as morphology, specific blood brain barrier enzyme markers, and tight intercellular junctions. The cells can also be used for the study of passive diffusion, carrier mediated transport, and metabolism to specific factors affecting the blood brain barrier permeability. However, passaging of brain microvessel endothelial cells results in loss of specific endothelial and blood brain barrier markers as well as tight intercellular junctions (Brightman and Neuwelt (ed.), Implications of the blood-brain barrier and its manipulation, Vol. 1, Plenum Medical, New York, pp. 53-83 (1989)).

Currently, primary cultures of brain microvessel endothelial cells are the principal tool for in vitro prediction of blood brain barrier permeability. Isolated and cultured primary brain cells developed previously have exhibited different properties primarily due to considerable variability in the starting material. For example, with respect to transcellular transport, rigorous comparison of data between different laboratories has been very difficult (Pardridge et al., Comparison of in vitro and in vivo models of drug transcytosis through the blood-brain barrier, J. Pharmacol. Exp. Thera. 253, 884-891 (1990); Masereeuw et al., In vitro and in vivo transport of zidovudine (AZT) across the blood-brain barrier and the effect of transport inhibitors. Pharm. Res., 11, 324-330 (1994)). Passaging primary cells can affect the differentiation of cells and lead to the selection of the most rapidly proliferating clones. Furthermore, the expression of some marker enzymes such as gamma-glutamyl transpeptidase as well as tight junctional complexity has been shown to decrease with time in culture and passage number (Meresse et. al., Bovine brain endothelial cells express tight junctions and monoamine oxidase activity in long-term culture, J. Neuorchem. 53, 1363-1371 (1989)). Some transporter substrates have been demonstrated to accumulate in the brain (see U.S. Pat. No. 6,489,302).

Thus, it is apparent that the presently available clones of immortalized brain microvessel endothelial cell cultures suffer from individual drawbacks in terms of phenotype expression and homogeneic maintenance of that expression. This leads to difficulties with respect to accuracy and reproducibility in studies utilizing brain microvessel endothelial cells to model passage of chemical compounds and moieties, e.g., potential therapeutic compounds and/or drug moieties, across the blood brain barrier.

SUMMARY

Disclosed herein are methods of screening agents, conjugates or conjugate moieties for the ability to enter the CNS by crossing the blood brain barrier in order to treat or diagnose conditions within the CNS. These methods entail providing a cell expressing an MCT1 transporter, the transporter being situated in the plasma membrane of the cell. The cell is contacted with an agent, conjugate or conjugate moiety. Whether the agent, conjugate or conjugate moiety passes through the plasma membrane via the MCT1 transporter is determined. If the method comprises contacting the cell with an agent, the agent is a neuropharmaceutical agent or an imaging component. If the method comprises contacting the cell with, a conjugate, the conjugate comprises an agent that is a neuropharmaceutical agent or an imaging component. If the method comprises contacting the cells with a conjugate moiety, the method further comprises linking the conjugate moiety to an agent that is a neuropharmaceutical agent or an imaging component. In some methods, the agent is other than a chemotherapeutic agent, an imaging agent or other agent used for treating or diagnosing cancer.

In some methods, if the agent is a cytotoxic agent or an imaging component, the method further comprises administering the agent, conjugate, or conjugate moiety to a peripheral tissue of an animal and measuring the amount of agent, conjugate, or conjugate moiety that passes through the blood brain barrier into the brain of the animal. In other methods, if the agent is a cytotoxic agent or an imaging component, the method further comprises contacting the agent to one side of a polarized monolayer of brain microvessel endothelial cells; and determining whether the agent is transported across the polarized monolayer.

In some methods, the cell endogenously expresses an MCT1 transporter. In other methods a nucleic acid molecule encoding an MCT1 transporter has been transfected or injected into the cell. In some methods the cell is a brain microvessel endothelial cell. In other methods the cell is an oocyte. In other methods the cell is a human embryonic kidney (HEK) cell. In other methods the cell is a Madin Darby canine kidney cell (MDCK). In still other methods, the cell is constructed to conditionally express the transporter.

In some methods the agent, conjugate or conjugate moiety comprises a monocarboxylic acid, optionally with oxygen atoms or carbonyl groups at the alpha or beta carbon position. In some methods the agent, conjugate or conjugate moiety is administered to an undiseased animal and any toxic effects are determined. In some methods the neuropharmaceutical agent is a cytotoxic neuropharmaceutical agent selected from the group consisting of platinum, nitrosourea, a phosphoramide group that is selectively cytotoxic to brain tumor cells, nitroimidizole, and nitrogen mustard.

Disclosed herein are methods of screening agents, conjugates or conjugate moieties for the ability to enter the CNS by crossing the blood brain barrier wherein a cell used for testing is a brain microvessel endothelial cell that is one of a plurality of brain microvessel endothelial cells forming a polarized monolayer. An agent, conjugate or conjugate moiety is contacted to one side of the polarized monolayer and whether the agent, conjugate or conjugate moiety is transported into the brain microvessel endothelial cells or to the opposite side of the polarized monolayer is determined. Some methods further comprise administering the agent, conjugate, or conjugate moiety to a peripheral tissue of an animal and measuring the amount of agent, conjugate, or conjugate moiety that passes through the blood brain barrier into the brain of the animal.

Disclosed herein are methods of screening an agent, conjugate or conjugate moiety for neuropharmacological activity useful for treating neurological disorders. In these methods, one determines whether the agent, conjugate or conjugate moiety is transported through an MCT1 transporter. One then administers the agent, conjugate or conjugate moiety to a test animal and determines whether the agent, conjugate or conjugate moiety is actively transported across the blood brain barrier by measuring agent, conjugate or conjugate moiety concentrations found in the CNS of the animal. For those agents, conjugates or conjugate moieties that are transported in sufficient quantities, the agents, conjugates or conjugate moieties can be further tested in animals suffering from a particular neurological disorder to determine whether the agents, conjugates or conjugate moieties have the requisite therapeutic neuropharmacological activity for treating such neurological disorder.

Also disclosed herein are methods for in vitro screening of agents, conjugates or conjugate moieties for improved retention in the CNS. In these methods, one determines the substrate properties of a compound on both uptake transporters and efflux transporters. An agent, conjugate or conjugate moiety is first tested for activity on the MCT1 transporter. The agent, conjugate or conjugate moiety is then tested for substrate activity on an efflux transporter, such as P Glycoprotein (PgP). Those agents, conjugates or conjugate moieties active on both the efflux transporter and MCT1 are then modified and tested for a reduction of efflux substrate activity and retested for retention of activity on the MCT1 transporter. This iterative process produces an agent, conjugate or conjugate moiety with an increased ratio of substrate activities in the uptake and efflux systems, and improved retention of pharmacological levels of the modified agent, conjugate or conjugate moiety in the CNS.

Disclosed herein are methods of screening an agent, conjugate or conjugate moiety for capacity to be transported into the brain, comprising determining whether the agent, conjugate or conjugate moiety specifically binds to an MCT1 transporter, contacting the agent to one side of a polarized monolayer of cells, and determining whether the agent is actively transported across the polarized monolayer. In some methods the specific binding is determined by contacting a cell expressing the MCT1 transporter, the transporter being situated in the plasma membrane of the cell, with a substrate of the MCT1 transporter, and determining whether the agent inhibits transport of the substrate across the polarized monolayer.

Disclosed herein are pharmaceutical compositions comprising a therapeutic neuropharmaceutical agent, a cytotoxic neuropharmaceutical agent or an imaging component linked to a conjugate moiety to form a conjugate in which the conjugate moiety has a higher $V_{max}$ for the MCT1 transporter than the therapeutic neuropharmaceutical agent, cytotoxic neuropharmaceutical agent or imaging component alone. Some pharmaceutical compositions have at least 5 times the $V_{max}$ for MCT1 than the neuropharmaceutical agent or the imaging component alone. In some pharmaceutical compositions the conjugate has a $V_{max}$ for MCT1 that is at least 5% of the $V_{max}$ for MCT1 of a compound selected from the group comprising lactic acid, pyruvic acid, nicotinic acid, 2-thiophene glyoxylate, pravastatin, butyric acid, salicylic acid, and carindicillin. In some pharmaceutical compositions the conjugate has a lower $V_{max}$ for an efflux transporter than the neuropharmaceutical agent or the imaging component alone. In some pharmaceutical compositions, the agent is not a cytotoxic agent, an imaging agent or other agent used for treating or diagnosing cancer.

Disclosed herein are methods of formulating a therapeutic neuropharmaceutical agent, a cytotoxic neuropharmaceutical agent or an imaging component. These methods entail linking the therapeutic neuropharmaceutical agent, the cytotoxic neuropharmaceutical agent or the imaging component to a conjugate moiety to form a conjugate, wherein the conjugate moiety has a greater $V_{max}$ for an MCT1 transporter than the component alone. The conjugate is formulated with a pharmaceutical carrier as a pharmaceutical composition. In some methods, the agent is not a cytotoxic agent, an imaging agent or other agent used for treating or diagnosing cancer.

Disclosed herein are methods of delivering a therapeutic neuropharmaceutical agent, a cytotoxic neuropharmaceutical agent or an imaging component. The methods involve administering to a patient a pharmaceutical composition comprising a therapeutic neuropharmaceutical agent, a cytotoxic neuropharmaceutical agent or an imaging component linked to a conjugate moiety to form a conjugate, wherein the conjugate has a higher $V_{max}$ for an MCT1 transporter than the therapeutic neuropharmaceutical agent, cytotoxic neuropharmaceutical agent or imaging component alone, whereby the conjugate passes through brain microvessel endothelial cells which make up the blood brain barrier, via the MCT1 transporter, into the CNS of the patient. Also disclosed herein are methods of delivering a conjugate, comprising administering to a patient a pharmaceutical composition comprising a neuropharmaceutical agent or imaging component linked to a conjugate moiety to form the conjugate, wherein the conjugate has a higher $V_{max}$ for an MCT1 transporter than the neuropharmaceutical agent or imaging component alone. In some methods the $V_{max}$ of the conjugate is at least two-fold higher than that of the neuropharmaceutical agent or imaging component alone. In some methods the neuropharmaceutical agent is a cytotoxic neuropharmaceutical selected from the group consisting of platinum, nitrosourea, a phosphoramide group selectively cytotoxic to brain tumor cells, nitroimidizole, and nitrogen mustard. In some methods, the agent is not a cytotoxic agent, an imaging agent or other agent used for treating or diagnosing cancer.

Disclosed herein are methods of treating neurological disorders. These methods entail administering to a patient an effective amount of an agent that is transported by MCT1, wherein the agent is a conjugate comprising a therapeutic neuropharmaceutical agent, a cytotoxic neuropharmaceutical agent or an imaging component linked to a conjugate moiety.

Disclosed herein are methods of screening an agent for decreased side effects in the central nervous system (CNS), comprising providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one efflux transporter protein that transports substrates out of the CNS, contacting the cell with the modified agent, and determining whether the modified agent is transported by the at least one efflux transporter protein with a higher $V_{max}$ than the agent, a higher $V_{max}$ indicating that the modification increases the capacity of the modified agent relative to the agent to be transported out of the CNS, thereby decreasing undesired side effects in the CNS.

BRIEF DESCRIPTION OF THE FIGURES

FIG. 1 shows the structures of known substrates of the MCT1 transporter.

FIG. 10 show the results of uptake experiments with (A) $^{14}$C-lactate and (B) 2-thiopheneglyoxylic acid by an LLCPK-TREx cell line expressing hMCT1. hMCT1 expression was induced by addition of tetracycline (tet). Negative control values were determined by measuring the uptake into non-tet treated (un-induced) and parental LLCPK cells.

FIG. 13 show competition binding and transport of $^{14}$C-lactate against eight MCT1 substrates (designated 1-8 in the upper part of the figure). Competition binding and transport assays were performed on LLPCK cells expressing endogenous hMCT1 (left bar in each set), an inducibly-expressed hMCT1-CD147 fusion protein (middle bar in each set) and a constitutively-expressed hMCT1-rCD147 fusion protein (right bar in each set).

DEFINITIONS

Figure 2:
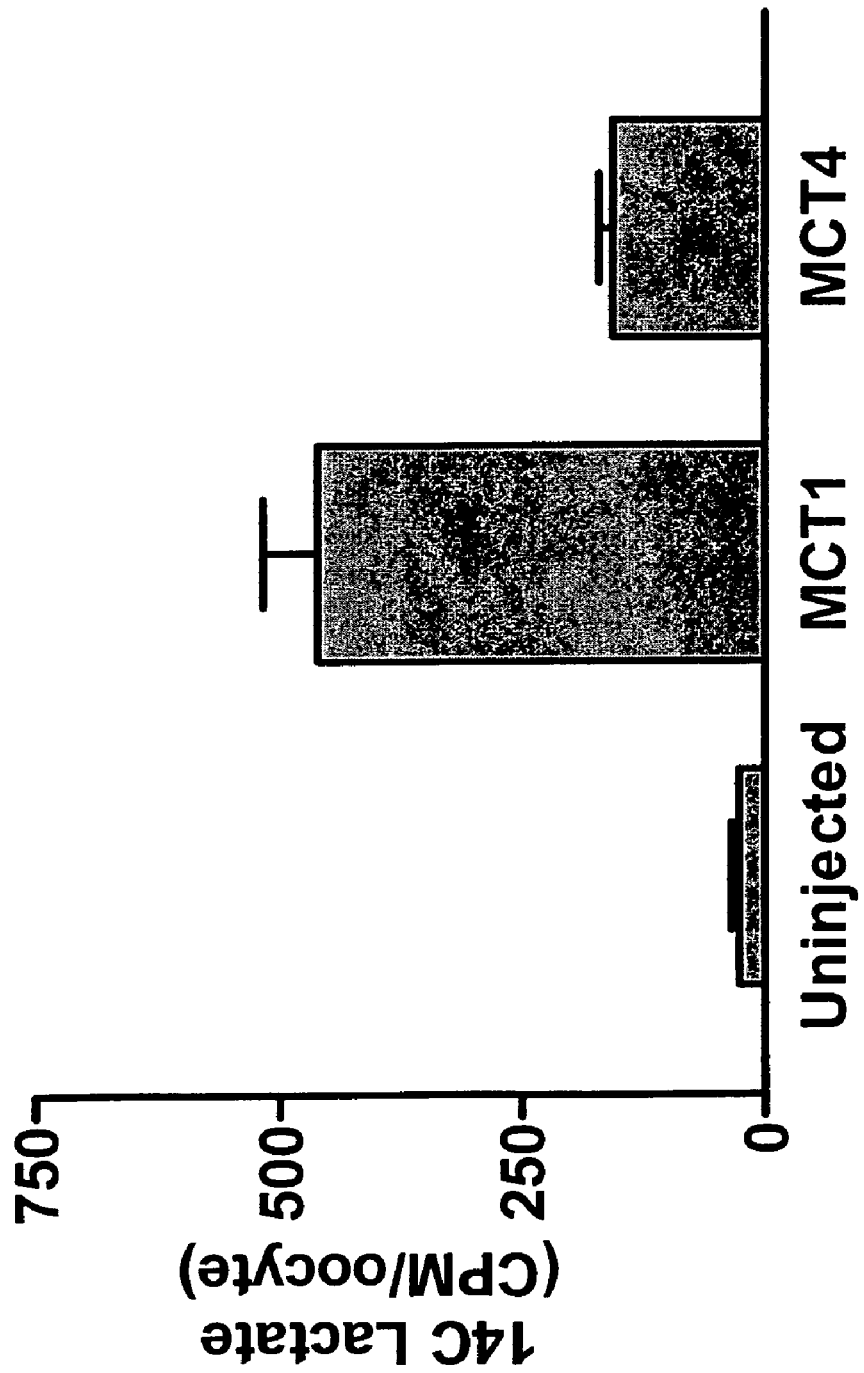
FIG. 2 shows oocyte uptake of $^{14}$C-lactate in oocytes injected with MCT1 and MCT4 cRNA.

"Transport by passive diffusion" refers to transport of an agent that is not mediated by a specific transporter protein. An agent that is substantially incapable of passive diffusion has a permeability across a standard cell monolayer (e.g., Caco-2 or MDCK cells or an artificial bilayer (PAMPA)) of less than $5 \times 10^{-6}$ cm/sec, and usually less than $1 \times 10^{-6}$ cm/sec in the absence of an efflux mechanism.

A "substrate" of a transporter protein is a compound whose uptake into or passage through the plasma membrane of a cell is facilitated at least in part by a transporter protein.

The term "ligand" of a transporter protein includes compounds that bind to the transporter protein. Some ligands are transported and are thereby also substrates. Some ligands inhibit or antagonize transport of a substrate by the transporter protein. Some ligands bind in a manner non-competitive with substrates and modulate the transport of substrates by the transporter protein.

The term "neuropharmaceutical agent" is used to describe a compound that has or may have a pharmacological activity in the treatment or prophylaxis of a neurological disorder. Neuropharmaceutical agents include compounds that are known drugs, compounds for which pharmacological activity has been identified but which are undergoing further therapeutic evaluation, and compounds that are members of collections and libraries that are to be screened for a pharmacological activity. The neuropharmaceutical agent can be a compound having a therapeutic, prophylactic or cytotoxic effect on a neurological disease including any condition which affects biological functioning of the central nervous system. Examples of neurological diseases include cancer (e.g., brain tumors), Acquired Immune Deficiency Syndrome (AIDS), stroke, epilepsy, Parkinson's disease, multiple sclerosis, neurodegenerative disease, trauma, depression, Alzheimer's disease, migraine, pain, or a seizure disorder. Classes of neuropharmaceutical agents include proteins, antibiotics, adrenergic agents, anticonvulsants, small molecules, nucleotide analogs, chemotherapeutic agents, anti-trauma agents, peptides and other classes of agents used in treatment or prophylaxis of a neurological disorder. Examples of proteins include CD4 (including soluble portions thereof), growth factors (e.g., nerve growth factor and interferon), dopamine decarboxylase and tricosanthin. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides are somatostatin analogues and enkephalinase inhibitors. Nucleotide analogs which can be used include azido thymidine (hereinafter AZT), dideoxy Inosine (ddI) and dideoxy cytodine (ddC).

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

An agent is "orally active" if it can exert a pharmacological activity when administered via an oral route.

A "peripheral tissue" means a tissue other than the CNS.

A "conjugate" refers to a compound comprising a neuropharmaceutical agent or imaging component and a chemical moiety bound thereto, which moiety by itself or in combination with the neuropharmaceutical agent or imaging component renders the conjugate a substrate for active transport, for example rendering the conjugate to be a substrate for a transporter protein. The chemical moiety may or may not be subject to cleavage from the neuropharmaceutical agent or imaging component upon uptake and metabolism of the conjugate in the patient's body. In other words, the moiety may be cleavably bound to the neuropharmaceutical agent or imaging component or non-cleavably bound to the neuropharmaceutical agent or imaging component. The bond can be a direct (i.e., covalent) bond or the bond can be through a linker. In cases where the bond/linker is cleavable by metabolic processes, the neuropharmaceutical agent or imaging component, or a further metabolite of the neuropharmaceutical agent or imaging component, is the therapeutic or imaging entity. In cases where the bond/linker is not cleavable by metabolic processes, the conjugate itself is the therapeutic or imaging entity. Most typically, the conjugate comprises a prodrug having a metabolically cleavable moiety, where the conjugate itself does not have pharmacological activity but the component to which the moiety is cleavably bound does have pharmacological activity. Typically, the moiety facilitates therapeutic use of the neuropharmaceutical agent or imaging component by promoting uptake of the conjugate via a transporter. Thus, for example, a conjugate comprising a neuropharmaceutical agent and a conjugate moiety may have a $V_{max}$ for a transporter that is at least 2, 5, 10, 20, 50 or 100-fold higher than that of the neuropharmaceutical agent or imaging component alone. A conjugate moiety can itself be a substrate for a transporter or can become a substrate when linked to the neuropharmaceutical agent or imaging component. Examples of preferred conjugate moieties are lactic acid, pyruvic acid, nicotinic acid, 2-thiophene glyoxylate, pravastatin, butyric acid, salicylic acid, and carindicillin. Thus, a conjugate formed from a neuropharmaceutical agent or imaging component and a conjugate moiety can have higher CNS uptake activity than either the neuropharmaceutical agent, the imaging component, or the conjugate moiety alone.

A "neuropharmacological" activity means that a neuropharmaceutical agent exhibits an activity in a screening system that indicates that the neuropharmaceutical agent is or may be useful in the prophylaxis or treatment of a neurological disease. The screening system can be in vitro, cellular, animal or human. Neuropharmaceutical agents can be described as having neuropharmacological activity notwithstanding that further testing may be required to establish actual prophylactic or therapeutic utility in treatment of a disease.

$V_{max}$ and $K_m$ of a compound for a transporter are defined in accordance with convention. $V_{max}$ is the number of molecules of compound transported per second at saturating concentration of the compound. $K_m$ is the concentration of the compound at which the compound is transported at half of $V_{max}$. When the goal is to transport an agent, conjugate or conjugate moiety into the CNS, a high $V_{max}$ for an influx transporter such as MCT1 is generally desirable. Likewise for the same goal, a low value of $K_m$ is typically desirable for transport of a compound present at low blood concentrations. In some cases a high value of $K_m$ is acceptable for the transport of compounds present at high concentrations in the blood. For these reasons, the intrinsic capacity of a compound to be transported by a particular transporter is usually expressed as the ratio $V_{max}$ of the compound/$V_{max}$ of a reference compound known to be a substrate for the transporter. $V_{max}$ is affected both by the intrinsic turnover rate of a transporter (molecules/transporter protein) and transporter density in the plasma membrane, which depends on expression level. In certain instances, the goal is to avoid transport into the CNS. In these instances, low $V_{max}$ for all influx transporters and a high $V_{max}$ for all efflux transporters expressed in the blood brain barrier is desirable.

"EC50", or "effective concentration 50", is a measurement of the substrate concentration that results in a turnover rate 50% of the maximal turnover rate for the substrate ($0.5 V_{max}$).

A plasma membrane containing a monolayer of cells in physical contact with each other and having different sets of proteins embedded in the plasma membranes facing either side of the monolayer is described as being "polarized". For example, brain microvessel endothelial cells in the blood brain barrier have a luminal side facing capillaries and exposed to blood, and an abluminal side facing cells of the central nervous system and exposed to cerebrospinal fluid. The luminal plasma membrane contains a different set of transmembrane and membrane-associated components than the abluminal plasma membrane of the same cell. Brain microvessel endothelial cells in culture can also be polarized, where the cells form a monolayer in culture that has a luminal and abluminal side. MDCK cells, when grown on filter membranes in transwell dishes, form a polarized monolayer in which one side of the monolayer is the apical side and the other is the basolateral side.

"Sustained release" refers to release of a therapeutic or prophylactic amount of a drug or an active metabolite thereof over a period of time that is longer than a conventional formulation of the drug. For oral formulations, the term "sustained release" typically means release of the drug within the GI tract lumen over a period of from about 2 to about 30 hours, more typically over a period of about 4 to about 24 hours. Sustained release formulations achieve therapeutically effective concentrations of the drug in the systemic blood circulation over a prolonged period of time relative to that achieved by oral administration of a conventional formulation of the drug. "Delayed release" refers to release of the drug or an active metabolite thereof into the gastrointestinal lumen after a delay time period, typically a delay of about 1 to about 12 hours, relative to that achieved by oral administration of a conventional formulation of the drug.

The phrase "specifically binds" when referring to a substrate or ligand of an MCT1 transporter refers to a specific interaction between a substrate or ligand and the MCT1 transporter in which the substrate or ligand binds preferentially with an MCT1 transporter and does not bind in a significant amount to most or any other proteins present in a biological sample. A substrate or ligand that specifically binds to an MCT1 transporter often has an association constant of $10$-$10^3$ $M^{-1}$, $10^5 M^{-1}$, $10^6 M^{-1}$ or $10^7 M^{-1}$, preferably $10^8 M^{-1}$ to $10^9 M^{-1}$ or higher. However, some substrates or ligands of MCT1 transporters have much lower affinities and yet the binding can still be shown to be specific. Substrates of MCT1 can specifically bind to MCT1 and other proteins such as efflux transporters without specifically binding to other proteins.

"$P_{app}$", or "apparent permeability", is a value that reflects the permeability of a test compound through a cell layer such as a polarized monolayer. The equation for determining $P_{app}$ is as follows:

$$P_{app} = \frac{V \cdot dC}{A \cdot C_0 \cdot dt} \text{(cm/sec)}$$

where,

V=volume of receiving chamber (in $cm^3$, i.e., ml);

dC/dt=steady state rate of appearance of applied compound in receiving chamber after primary lag time (in µM/sec);

$C_0$=concentration of compound in the donor chamber (in µM)

A=area of the cell layer (in $cm^2$)

"Allelic variants" at the DNA level are the result of genetic variation between individuals of the same species. Some allelic variants at the DNA level that cause substitution, deletion or insertion of amino acids in proteins encoded by the DNA result in corresponding allelic variation at the protein level.

"Cognate forms" of a gene refers to variation between structurally and functionally related genes between species. For example, the human gene showing the greatest sequence identity and closest functional relationship to a mouse gene is the human cognate form of the mouse gene.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope hereof, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLASTN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION

I. General

MCT1 is shown herein to be expressed at high levels in brain microvessel endothelial cells. This finding can be used to generate or isolate conjugates and agents having neuropharmacological or imaging activity useful for treatment, prophylaxis or diagnosis of neurological diseases. The invention provides methods of identifying agents, conjugates or conjugate moieties that are substrates for MCT1. For therapeutic purposes, agents or conjugates having inherent neuropharmacologic activity can be screened to determine whether they are substrates for MCT1. Alternatively, a conjugate moiety lacking such activity can be screened, and linked to a neuropharmacologic agent after screening. Agents or conjugates that both have neuropharmacologic activity and are substrates for MCT1 are preferentially transported into the CNS via MCT1 transporters after administration to a patient. Such an agent or conjugate by itself or in combination with another agent is effective in treatment or prophylaxis of a neurological disease. An analogous approach is used for imaging features of the brain. Agents and conjugates that have an imaging component and are substrates for MCT1 are preferentially transported into the CNS via MCT1 transporters. The imaging component is then detected by various methods such as detecting radioactive decay of the imaging component. The agents and conjugates can be used to image brain tumors overexpressing the MCT1 transporter. Optionally, the agents or conjugates have inherent affinity for, or are provided with a conjugate moiety that confers affinity for, a particular antigen or cell type within the brain. For example, the agents or conjugates can be provided with a targeting moiety to Aβ to allow imaging of plaques in Alzheimer's patients.

II. MCT1 Transporter

The family of monocarboxylate transporters (MCTs) contains at least 14 members in humans (SLC16A1-14). Monocarboxylate transporters have 12 putative transmembrane domains, with both the amino and carboxy termini located on the cytoplasmic side. A sub-family of monocarboxylate transporters (MCT1, MCT2, MCT4) are specialized for the transport of metabolic intermediates and cofactors such as lactic acid, pyruvic acid, and nicotinic acid, whereas other members (MCT8, MCT11) transport amino acids and thyroid hormones. It has been reported that MCT1 contributes to the intestinal absorption of xenobiotic drugs such as salicylic acid, pravastatin, and antibiotics. It has been reported that MCT1 co-assembles with the glycoprotein CD147. MCT1 is a proton-coupled transporter that cotransports the a monocarboxylate molecule and a proton.

It is now shown that MCT1 is highly expressed in brain microvessel endothelial cells. MCT1 is expressed at a level more than 10-fold higher than other MCT family transporters with similar substrate specificity. It is desirable to generate agents, conjugates, and conjugate moieties for transport into the CNS that have activity for MCT1 due to this high expression level. The GenBank accession number for human MCT1 is NM-003051 SEQ ID NO:1). Unless otherwise apparent from the context, reference to a transporter includes the amino acid sequence described in or encoded by the GenBank reference number NM-003051, and, allelic, cognate and induced variants and fragments thereof retaining essentially the same transporter activity. Usually such variants show at least 90% sequence identity to the exemplary Genbank nucleic acid or amino acid sequence.

III. Methods of Screening to Identify MCT1 Substrates

Agents known or suspected to have a neuropharmaceutical activity or to comprise an imaging component can be screened directly for their capacity to act as substrates of MCT1. Alternatively, conjugate moieties can be screened as substrates, and the conjugate moieties are then linked to a neuropharmaceutical agent or imaging component. In such methods, the conjugate moieties can optionally be linked to a neuropharmaceutical agent or imaging component, or other molecule during the screening process. If another molecule is used in place of a neuropharmaceutical agent or imaging component, the molecule can be chosen to resemble the structure of a neuropharmaceutical agent or imaging component ultimately intended to be linked to the conjugate moiety for neuropharmaceutical use. Alternatively, a conjugate moiety can be screened for a substrate activity alone and linked to a neuropharmaceutical agent or imaging component after screening.

Preferred substrates for MCT1 are monocarboxylic acids, optionally with oxygen atoms or carbonyl groups at the alpha or beta carbon position. Table 1 lists examples of substrates of MCT1. The structures of each compound listed in Table 1 are depicted in FIG. 1.

TABLE 1

| SUBSTRATES | Reported Affinity for MCT1 |
|---|---|
| Lactic Acid | 2 mM |
| Pyruvic Acid | 1 mM |
| Nicotinic Acid | 4 mM |
| Butyric Acid | 8 mM |
| 2-Thiophene glyoxylate | 3 mM |
| Pravastatin | >5 mM |
| Salicylic Acid | >5 mM |
| Carindicillin | >5 mM |
| Sulfasalazine | 0.15 mM |
| Phloretin | 0.2 mM |

Lactic acid (including lactate), pyruvic acid, nicotinic acid, 2-thiophene glyoxylate, pravastatin, butyric acid, salicylic acid, and carindicillin are examples of MCT1 substrates that are candidates for conjugation to therapeutic neuropharmaceutical agents, cytotoxic neuropharmaceutical agents and imaging components.

In some screening methods, the cells are transfected with DNA encoding the MCT1 transporter. HEK (human embryonic kidney) and CHO (Chinese hamster ovary) cells, for example, are suitable for transfection. Oocytes can be injected with MCT1 cRNA to express MCT1 transporter. In some methods, the only transporter expressed by the cells is the MCT1 transporter. In other methods, cells express MCT1 in combination with other transporters. In still other methods, agents, conjugate moieties or conjugates are screened on different cells expressing different transporters. Agents, conjugate moieties or conjugates can be screened either for specificity for the MCT1 transporter or for transport into cells endogenously expressing a plurality of transporters. In some methods, the results of a screening method (e.g., a competition uptake, exchange or direct uptake assay) using a cell expressing the MCT1 transporter can be compared with the results of a control cell(s) lacking the MCT1 transporter or in the presence of a specific inhibitor of the MCT1 transporter.

In some methods, cells endogenously expressing the MCT1 transporter are used. Brain microvessel endothelial cells, for example, endogenously express the MCT1 transporter, as demonstrated in Example 1. Agents, conjugate moieties or conjugates can be screened for transport into cultured brain microvessel endothelial cells. Passaging cultures of brain microvessel endothelial cells typically causes the cells to lose differentiation characteristics such as the ability to form tight junctions. The propensity of passaged cells to lose differentiation characteristics can be avoided through the use of brain microvessel endothelial cells that are transformed with an SV40 large T antigen. See Terasaki et al., Drug Discovery Today 8:944-954 (2003). Inducible expression of the SV40 large T antigen allows cells to divide when the antigen is expressed and differentiate when the antigen is not expressed. Brain microvessel endothelial cells can be isolated from animals transgenic for the SV40 large T antigen, which can be expressed in a temperature-sensitive fashion. The cells are stimulated to divide by being cultured at the temperature at which the antigen is expressed. Once the cells have formed a monolayer, they are placed at a temperature at which the antigen is not expressed, causing the cells to stop dividing and differentiate. Differentiation results in the formation of tight junctions and the polarization of the plasma membranes. Monolayers of polarized cells are tested for the ability to transport agents, conjugates or conjugate moieties. In other methods, the ability to transport agents, conjugates or conjugate moieties is measured by administering the agent, conjugate, or conjugate moiety to a peripheral tissue of an animal. The amount of agent, conjugate, or conjugate moiety that passes through the blood brain barrier into the brain of the animal is measured either in the cerebral spinal fluid (CSF) or in whole brain tissue following brain perfusion with solution to remove compound from the brain vasculature. Generally, the brain penetration of the drug is reported as the ratio of the unbound compound in brain tissue or CSF to the unbound compound in the blood. In some methods, the measurement can be made on a specimen from the animal or in situ.

In some methods, the ability of an agent, conjugate or conjugate moiety to specifically bind to an MCT1 transporter is tested. A known substrate of the MCT1 transporter and the agent, conjugate or conjugate moiety are added to cells expressing the MCT1 transporter. The amount or rate of transport of the substrate in the presence of the agent, conjugate or conjugate moiety is compared to the amount or rate of transport of the agent, conjugate or conjugate moiety in the absence of the test compound. If the amount or rate of transport of the substrate is decreased by the presence of the agent, conjugate or conjugate moiety, the agent, conjugate or conjugate moiety binds the MCT1 transporter. Agents, conjugates or conjugate moieties that bind the MCT1 transporter can be further analyzed to determine if they are transported by the MCT1 transporter or only adhere to the exterior of the transporter. Agents, conjugates or conjugate moieties that are transported by the MCT1 transporter can be further tested to determine if they are transported from one side of a monolayer of polarized cells to the other side, such as a monolayer of brain microvessel endothelial cells. Agents and conjugates having neuropharmaceutical activity and that that are transported by the MCT1 transporter can be used to form pharmaceutical compositions. Conjugate moieties that are transported by the MCT1 transporter can be linked to a therapeutic or cytotoxic neuropharmaceutical agent or an imaging component.

Transport of a compound into a cell can be detected by detecting a signal from within a cell from any of a variety of reporters. The reporter can be as simple as a label such as a fluorophore, a chromophore, or a radioisotope. Confocal imaging can also be used to detect internalization of a label as it provides sufficient spatial resolution to distinguish between fluorescence on a cell surface and fluorescence within a cell; alternatively, confocal imaging can be used to track the movement of compounds over time. In another approach, transport of a compound is detected using a reporter that is a substrate for an enzyme expressed within a cell. Once the compound is transported into the cell, the substrate is metabolized by the enzyme and generates an optical signal that can be detected. Light emission can be monitored by commercial PMT-based instruments or by CCD-based imaging systems. In addition, assay methods utilizing liquid chromatography-mass spectroscopy (LC-MS-MS) detection of the transported compounds or electrophysiological signals indicative of transport activity are also employed. Mass spectroscopy is a powerful tool because it allows detection of very low concentrations of almost any compound, especially molecules for which a radiolabeled version is not available. It can also be used to distinguish substrates from nontransported ligands. These same detection methods can be used to determine if a compound is transported from one side of a monolayer of polarized cells to the other side by administering the compound to one side of the monolayer and sampling the media on the other side of the monolayer after a predetermined period of time.

In some methods, multiple agents, conjugates or conjugate moieties are screened simultaneously and the identity of each agent, conjugate or conjugate moiety is tracked using tags linked to the agents, conjugates or conjugate moieties. In some methods, a preliminary step is performed to determine binding of an agent, conjugate or conjugate moiety to a transporter. Although not all agents, conjugates or conjugate moieties that bind to a transporter are substrates of the transporter, observation of binding is an indication that allows one to reduce the number of candidates from an initial repertoire. In some methods, the transport rate of an agent, conjugate or conjugate moiety is tested in comparison with the transport rate of a reference substrate for that transporter. For example, lactate, a natural substrate of MCT1, can be used as a reference. The comparison can be performed in separate parallel assays in which an agent, conjugate or conjugate moiety under test and the reference substrate are compared for uptake on separate samples of the same cells. Alternatively, the comparison can be performed in a competition format in which an agent, conjugate or conjugate moiety under test and the reference substrate are applied to the same cells. Typically, the agent, conjugate or conjugate moiety and the reference substrate are differentially labeled in such assays.

In comparative assays, the $V_{max}$ of an agent, conjugate or conjugate moiety tested can be compared with that of a reference substrate. If an agent, conjugate moiety or conjugate has a $V_{max}$ of at least 1%, 5%, 10%, 20%, and most preferably at least 50% of the reference substrate for the MCT1 transporter, then the agent, conjugate moiety or conjugate is also a substrate for the MCT1 transporter. If transport of the agent, conjugate moiety or conjugate into the CNS is desired, a higher $V_{max}$ of the agent, conjugate moiety or conjugate relative to that of the reference substrate is preferred. Therefore, agents, conjugate moieties or conjugates having $V_{max}$'s of at least 1%, 5%, 10%, 20%, 50%, 100%, 150% or 200% (i.e., two-fold) of the $V_{max}$ of a reference substrate (e.g., lactate) for the transporter are screened in some methods. The components to which conjugate moieties are linked can by themselves show little or no detectable substrate activity for the transporter (e.g., $V_{max}$ relative to that of a reference substrate of less than 0.1% or 1%). Preferred agents, conjugates or conjugate moieties have a $V_{max}$ for MCT1 that is at least 5% of the $V_{max}$ for MCT1 of lactate. Preferred conjugates comprising a neuropharmaceutical agent or imaging component linked to a conjugate moiety preferably have a greater $V_{max}$ for MCT1 than the neuropharmaceutical agent or imaging component alone.

Having determined that an agent, conjugate or conjugate moiety is a substrate for MCT1, a further screen can be performed to determine its therapeutic activity in treatment or prophylaxis of a disease, or its cytotoxic activity against brain tumor cells. Usually the disease is neurological (i.e., the pathology occurs in the CNS). Alternatively, the diseased tissue is non-CNS tissue but is responsive to treatment by an agent that exerts a pharmacological effect on the CNS that in turn causes an effect on the diseased non-CNS tissue, such as an effect caused by the release of hormones from the CNS. Diseases of this type are also considered to be diseases of the CNS unless otherwise apparent from context. If the agent, conjugate or conjugate moiety does not have inherent therapeutic or cytotoxic activity, it is first linked to another chemical component having such therapeutic or cytotoxic properties. The agent, conjugate or conjugate moiety is then contacted with cells expressing MCT1. The contacting can be performed either on a population of cells in vitro, or the brain microvessel endothelial cells of a test animal via administration of the agent, conjugate or conjugate moiety to a test animal. The therapeutic or cytotoxic activity of the agent, conjugate or conjugate moiety is then determined from established protocols for that particular disease. Optionally, the effect of the agent, conjugate or conjugate moiety can be compared with a placebo.

A further screen can be performed to determine toxicity of the agent, conjugate, or conjugate moiety to normal cells. The agent, conjugate or conjugate moiety is administered to a laboratory animal that is preferably in an undiseased state. Various tissues of the animal, such as liver, kidney, heart and brain are then examined for signs of pathology. Cells in the animal can also be analyzed for uptake of the agent, conjugate, or conjugate moiety.

IV. Iterative Modification and Testing of MCT1 Substrates

Having determined that an agent, conjugate or conjugate moiety is a substrate for MCT1, the agent, conjugate or conjugate moiety can be modified to improve its properties as a substrate. The modified agent, conjugate or conjugate moiety is then tested for transport by MCT1. Modified agents, conjugates or conjugate moieties that are transported by MCT1 at a higher $V_{max}$ compared to the unmodified agent, conjugate or conjugate moiety are preferred. The process of modifying agents, conjugates or conjugate moieties and testing for transport by MCT1 can be repeated until a desired level of transport is reached.

Agents, conjugates or conjugate moieties that are substrates of MCT1 can also be modified for decreased capacity to be transported out of cells by efflux transporters. An agent, conjugate or conjugate moiety transported by MCT1 is assayed to determine whether it is also a substrate for one or more efflux transporters. If the agent, conjugate or conjugate moiety is transported by an efflux transporter, the agent, conjugate or conjugate moiety is modified and tested for both reduced transport by an efflux transporter and retention of MCT1 substrate activity.

In some instances, the specific efflux transporter responsible for transporting an agent, conjugate or conjugate moiety is known. The agent, conjugate or conjugate moiety is modified, preferably by addition of a chemical group that differs in chemical characteristics from other known substrates of the efflux transporter. The modified agent, conjugate or conjugate moiety is then tested for retained capacity to be transported by MCT1 and a diminished capacity to be transported by an efflux transporter. It is not necessary that the modified agent, conjugate or conjugate moiety retain the same kinetic properties of MCT1 transporter substrate as the unmodified agent, conjugate or conjugate moiety as long as some MCT1 substrate activity is retained. Examples of efflux transporters are the P-glycoprotein (PgP), multidrug resistance protein (MRP1), and breast cancer resistance protein (BCRP). Preferred agents, conjugates or conjugate moieties have an MCT1 transport:efflux transport ratio of at least 1.1:1.0, more preferably, 2.0:1.0, and more preferably 5.0:1.0 and more preferably 10.0:1.0 or higher at a given concentration of agent, conjugate or conjugate moiety.

Efflux transporter activity can be measured in several ways. First, functional assays can be performed in which interaction of compounds with efflux transporters is measured by stimulation of efflux transporter ATPase activity in cellular membrane fragments or vesicles. Second, competition assays can be performed in which test compounds compete with known efflux substrates in whole cells. Third, direct transport assays can be performed in which the transport of compounds is measured across a polarized monolayer of cells. Other assays besides these three can also be used to directly or indirectly measure the efflux substrate characteristics of a test compound.

The efflux transporter ATPase assay is based on the fact that most efflux substrates increase the ATPase activity of efflux transporters upon binding. In one type of assay, Baculovirus membrane fragments or vesicles containing an efflux transporter such as PgP, as well as control membrane fragments or vesicles not containing the efflux transporter, are either prepared or obtained from commercial suppliers. The ATPase activity of the membrane fragments or vesicles is measured in the presence of various concentrations of the test compound. An agent, conjugate, or conjugate moiety that is transported by MCT1 is added to the ATPase assay reaction and the amount of ATPase activity is measured at various concentrations of agent, conjugate, or conjugate moiety. Parallel experiments are performed in which ATPase activity is measured under addition of the same concentrations of modified agent, conjugate, or conjugate moiety that retain MCT1 substrate activity. Reduced ATPase activity caused by the modified agent, conjugate, or conjugate moiety compared to the unmodified agent, conjugate, or conjugate moiety indicates that the modified agent, conjugate, or conjugate moiety is a better candidate for retention in the CNS.

In the competition assay, the test compound is assayed for competition with a known efflux substrate. For example, calcein-AM is a non-fluorescent compound that is a substrate of PgP and MRP1. Calcein-AM is initially loaded into the cells, for example, by transport by passive diffusion. Cells expressing these efflux transporters actively efflux nearly all of the calcein-AM that is present in the cells. However, when other efflux transporter substrates are present, these other substrates compete with calcein-AM for efflux, resulting in more calcein-AM accumulating inside the cells. Intracellular esterases convert the non-fluorescent calcein-AM to fluorescent calcein which can be measured spectrophotometrically. An agent, conjugate, or conjugate moiety that is transported by MCT1 is loaded into efflux transporter-containing cells by either MCT1 transport or passive diffusion. Calcein-AM is also loaded into the cells by active transport or transport by passive diffusion. Accumulation of calcein-AM is measured and compared to the amount of accumulation in the absence of the agent, conjugate, or conjugate moiety. Parallel experiments are performed in which a modified agent, conjugate, or conjugate moiety that is transported by MCT1 is loaded into the cells. Accumulation of calcein-AM is measured and compared to the amount of accumulation in the absence of the modified agent, conjugate, or conjugate moiety. Decreased calcein-AM accumulation inside the cells caused by the presence of a modified agent, conjugate, or conjugate moiety compared to calcein-AM accumulation in the presence of unmodified agent, conjugate, or conjugate moiety indicates that the modified agent, conjugate, or conjugate moiety is a better candidate for retention inside the CNS.

The cells used for competition assays can be cells that either express a high endogenous level of the efflux transporter of interest or are transformed with an expression vector containing the efflux transporter gene. Suitable cell lines for efflux assays are, for example, HEK and MDCK cell lines into which the PgP gene has been transfected, or MES-SA/Dx5 uterine sarcoma cells grown in the presence of 500 nM doxorubicin, which express a high endogenous level of PgP. These cells can optionally be transfected with the MCT1 transporter gene. Preferred cells express both one or more efflux transporter genes such as PgP and the MCT1 gene, either endogenously or through transfection of expression vectors.

A third type of efflux transporter assay is the cellular transwell monolayer efflux assay. In this assay, cells expressing efflux transporters, such as MDCK cells containing the TREx-PgP expression vector, are seeded and grown in transwell dishes on filter membranes made of substances such as polycarbonate. The cells form a polarized monolayer. The transwell dishes have apical and basolateral chambers that are separated by the filter membrane on which the polarized monolayer is situated. Assays are performed by placing a test compound in either the apical or basolateral chamber, followed by sampling the opposite chamber after a predetermined period of time such as 60-120 minutes and measuring the amount of the test compound. The test compound can be measured by methods such as radiolabel detection or LC-MS-MS analysis. Assays are performed in the presence and absence of an efflux transporter inhibitor or competitor. Efflux transporter inhibitors or competitors increase apical to basolateral transport and decrease basolateral to apical transport of compounds that are efflux transporter substrates. Apparent permeability ($P_{app}$) of test compounds is measured. Test compounds that are substrates of efflux transporters generate a $P_{app}$ (basolateral to apical)/$P_{app}$ (apical to basolateral) ratio of greater than 2.0, while test compounds that are not substrates generate a ratio of 1.5 or less. Test compounds that generate ratios between 1.5 and 2.0 require additional testing to determine if they are efflux transporter substrates. An agent, conjugate, or conjugate moiety that is an MCT1 substrate and also generates a ratio of greater than 2.0 can be modified. A modified agent, conjugate, or conjugate moiety that retains MCT1 substrate activity and generates a lower ratio compared to the unmodified agent, conjugate, or conjugate moiety indicates that the modified agent, conjugate, or conjugate moiety is a better candidate for retention inside the CNS.

An additional screen can be performed to determine whether agents, conjugates or conjugate moieties have substantial capacity for passive diffusion across the brain microvessel endothelial cells making up the blood brain barrier. Such an assay can be performed using cells lacking MCT1 transporters. That is, the agents, conjugates or conjugate moieties are exposed to cells that lack MCT1 transporters, and the amount of agents, conjugates or conjugate moieties that are present inside the cell is measured.

V. Modification of Compounds having Non-Neuropharmacologic Activity

In some instances it is desirable to modify an agent to reduce its capacity to be transported from the blood into the brain. Reduced capacity to enter the brain is desirable for agents having a pharmacological activity that is useful in a tissue outside the CNS, but which causes undesired side effects when the agent enters the CNS. Most typically, such agents are drugs administered to treat a non-neurological disease, and which exert a useful therapeutic pharmacological effect on cells, tissues, or molecules located outside of the CNS. When such drugs are transported from the blood into the brain, serious side effects can occur. Many known drugs exhibit undesirable side effects from penetrating the CNS. Examples include drowsiness experienced by patients taking antihistamines, nonsteroidal anti-inflammatory drugs (NSAIDS), anti-asthmatics and antihypertensives.

The methods are performed on an agent having an intended site of pharmacological activity that is located outside of the CNS. The agent is known or suspected to enter the CNS. In some instances, the agent is known to be transported by MCT1. The agent is covalently attached to a conjugate moiety and the resulting conjugate is tested for transport into the brain. The assay can be performed on brain microvessel endothelial cells, cells transformed with an MCT1 expression vector, a polarized monolayer of cells, or an actual blood brain barrier via administration to a test animal. Transport of the conjugate is then compared with transport of the agent alone (i.e., without the conjugate moiety). Conjugates having a lower $V_{max}$ for transport than the agent alone are less likely to exhibit undesirable CNS side effects caused by unwanted transport from the blood into the brain. For example, preferred conjugates include those having a lower $V_{max}$ for transport by MCT1 than the agent alone.

Some methods comprise providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one transporter protein that transports substrates across the blood brain barrier, contacting the cell with the modified agent, and determining whether the modified agent passes through the plasma membrane via the transporter protein with a lower $V_{max}$ than the agent, a lower $V_{max}$ indicating that the modification decreases the capacity of the modified agent relative to the agent to cross the blood brain barrier, thereby decreasing undesired side effects in the CNS. In some methods the at least one transporter protein is MCT1. In some methods the cell is transformed or injected with a nucleic acid encoding a transporter or the cell is a brain microvessel endothelial cell. In some methods the modifying step comprises linking the agent to a conjugate moiety to form a conjugate, preferably wherein the conjugate moiety is an inhibitor of the MCT1 transporter.

Other methods comprise providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one efflux transporter protein that transports substrates out of the CNS, contacting the cell with the modified agent, and determining whether the modified agent is transported by the at least one efflux transporter protein with a higher $V_{max}$ than the agent, a higher $V_{max}$ indicating that the modification increases the capacity of the modified agent relative to the agent to be transported out of the CNS, thereby decreasing undesired side effects in the CNS. In some methods the at least one efflux transporter protein is P-glycoprotein (PgP), multidrug resistance protein (MRP1), or breast cancer resistance protein (BCRP). In some methods the cell is transformed or injected with a nucleic acid encoding an efflux transporter or the cell is a brain microvessel endothelial cell, a kidney-derived cell, or a uterine sarcoma cell. In some methods the modifying step comprises linking the agent to a conjugate moiety to form a conjugate, preferably wherein the conjugate moiety is a substrate of the efflux transporter.

VI. Sources of Neuropharmaceutical Agents, Imaging Components, and Conjugate Moieties Therapeutic neuropharmaceutical agents, cytotoxic neuropharmaceutical agents, imaging components and conjugate moieties can be obtained from natural sources such as, e.g., marine microorganisms, algae, plants, and fungi. Alternatively, these compounds can be from combinatorial libraries, including peptides or small molecules, or from existing repertories of chemical compounds synthesized in industry, e.g., by the chemical, pharmaceutical, environmental, agricultural, marine, cosmeceutical, drug, and biotechnological industries. Neuropharmaceutical compounds can include proteins, antibiotics, adrenergic agents, anticonvulsants, small molecules, nucleotide analogs, chemotherapeutic agents, anti-trauma agents, peptides and other classes of agents used in treatment or prophylaxis of a neurological disease. Examples of such proteins include CD4 (including soluble portions thereof), growth factors (e.g., nerve growth factor and interferon), dopamine decarboxylase and tricosanthin. Examples of such antibiotics include amphotericin B, gentamycin sulfate, and pyrimethamine. Examples of such adrenergic agents (including blockers) include dopamine and atenolol. Examples of such chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of such peptides are somatostatin analogues and enkephalinase inhibitors. Nucleotide analogs which can be used include azido thymidine (hereinafter AZT), dideoxy Inosine (ddI) and dideoxy cytodine (ddC).

Typically if an agent is being screened as a substrate, the agent is known or suspected to have an inherent therapeutic neuropharmaceutical, cytotoxic neuropharmaceutical or imaging activity. If a conjugate is being screened, the conjugate usually comprises such an agent or component. If a conjugate moiety is being screened, the conjugate moiety typically lacks a therapeutic, cytotoxic or imaging activity and an agent or component that has this activity is added after screening.

Suitable cytotoxic agents for incorporation into conjugates or linkage to conjugate moieties after screening include platinum, nitrosourea, nitrogen mustard, nitroimidizole, and a phosphoramide group that is only cytotoxic to brain tumor cells. The choice of imaging component depends on the means of detection. For example, a fluorescent imaging component is suitable for optical detection. A paramagnetic imaging component is suitable for topographic detection without surgical intervention. Radioactive labels can also be detected using positron emission tomography or single photon emission computed tomography.

The agents, conjugates or conjugate moieties to be screened, optionally linked to a neuropharmaceutical agent or an imaging component if not inherently present, are preferably small molecules having molecular weights of less than 1000 Da and preferably less than 500 Da.

VII. Linkage of Neuropharmaceutical Agents or Imaging Components to Substrates

Conjugates can be prepared by either by direct conjugation of a neuropharmaceutical agent or an imaging component to a substrate of MCT1 with a covalent bond (optionally cleavable in vivo), or by covalently coupling a difunctionalized linker precursor with the neuropharmaceutical agent or imaging component and substrate. The linker precursor is selected to contain at least one reactive functionality that is complementary to at least one reactive functionality on the neuropharmaceutical agent or imaging component and at least one reactive functionality on the substrate. Optionally, the linker is cleavable. Suitable complementary reactive groups are well known in the art as illustrated below:

| COMPLEMENTARY BINDING CHEMISTRIES | | |
|---|---|---|
| First Reactive Group | Second Reactive Group | Linkage |
| hydroxyl | carboxylic acid | ester |
| hydroxyl | haloformate | carbonate |
| thiol | carboxylic acid | thioester |
| thiol | haloformate | thiocarbonate |
| amine | carboxylic acid | amide |
| hydroxyl | isocyanate | carbamate |
| amine | haloformate | carbamate |
| amine | isocyanate | urea |
| carboxylic acid | carboxylic acid | anhydride |
| hydroxyl | phosphorus acid | phosphonate or phosphate ester |

The same methods of chemical modification can be used to form conjugates for the purpose of inhibiting transport into the CNS, for inhibiting efflux from the CNS, or for enhancing efflux from the CNS.

VIII. Pharmaceutical Compositions

The above screening processes can identify one or more types of compounds that can be incorporated into pharmaceutical compositions. These compounds include agents that are both substrates for MCT1 and have an inherent neuropharmaceutical activity or imaging activity. The compounds also include conjugates in which a neuropharmaceutical agent or imaging component is linked to a substrate for MCT1. Conjugates comprising an agent with a pharmacological activity and a conjugate moiety having decreased substrate capacity for MCT1 relative to the agent alone are also provided for the purpose of reducing transport of the agent into the CNS, where the agent would confer undesired side effects.

One or more of the above entities can be combined with pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., Remington's Pharmaceutical Sciences, Mace Publishing Company, Philadelphia, Pa., 17th ed. (1985); for a brief review of methods for drug delivery, see, Langer, Science 249:1527-1533 (1990); each of these references is incorporated by reference in its entirety).

Pharmaceutical compositions can be administered orally, intranasally, intradermally, subcutaneously, intrathecally, intramuscularly, topically, intravenously, or injected directly to a site of cancerous tissue. For parenteral administration, the compounds disclosed herein can be administered as injectable dosages of a solution or suspension of the compound in a physiologically acceptable diluent with a pharmaceutical carrier which can be a sterile liquid such as water, oils, saline, glycerol, or ethanol. Additionally, auxiliary substances, such as wetting or emulsifying agents, surfactants, pH buffering substances and the like can be present in the pharmaceutical compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or a copolymer thereof for enhanced adjuvant effect, as discussed above (see Langer, Science 249, 1527 (1990) and Hanes, Advanced Drug Delivery Reviews 28, 97-119 (1997). The pharmaceutical compositions disclosed herein can be administered in the form of a depot injection or implant preparation which can be formulated in such a manner as to permit a sustained or pulsatile release of the active ingredient.

Pharmaceutical compositions for oral administration can be in the form of e.g., tablets, pills, powders, lozenges, sachets, cachets, elixirs, suspensions, emulsions, solutions, or syrups. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. Preserving agents such as methyl- and propylhydroxy-benzoates; sweetening agents; and flavoring agents can also be included. Depending on the formulation, compositions can provide quick, sustained or delayed release of the active ingredient after administration to the patient. Polymeric materials can be used for oral sustained release delivery (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J Macromol. Sci. Rev. Macromol Chem. 23:61; see also Levy et al., 1985, Science 228: 190; During et al., 1989, Ann. Neurol. 25:351; Howard et al., 1989, J. Neurosurg. 71:105). Sustained release can be achieved by encapsulating conjugates within a capsule, or within slow-dissolving polymers. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, Int. J. Pharm. Tech. & Prod. Mfr., 1984, 5(3) 1-9). Factors affecting drug release have been described in the art (Bamba et al., Int. J. Pharm., 1979, 2, 307). For administration by inhalation, the compounds for use according to the disclosures herein are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Effective dosage amounts and regimes (amount and frequency of administration) of the pharmaceutical compositions are readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The components of pharmaceutical compositions are preferably of high purity and are substantially free of potentially harmful contaminants (e.g., at least National Food (NF) grade, generally at least analytical grade, and more typically at least pharmaceutical grade).

To the extent that a given compound must be synthesized prior to use, the resulting product is typically substantially free of any potentially toxic agents, particularly any endotoxins, which may be present during the synthesis or purification process. Compositions are usually made -under GMP conditions. Compositions for parenteral administration are usually sterile and substantially isotonic.

IX. Methods of Treatments

Pharmaceutical compositions disclosed herein are used in methods of treatment of prophylaxis of neurological diseases. Examples of such diseases amenable to treatment are cancer (e.g., brain tumors), Acquired Immune Deficiency Syndrome (AIDS), stroke, epilepsy, Parkinson's disease, multiple sclerosis, neurodegenerative disease, trauma, depression, Alzheimer's disease, migraine, pain, seizure disorders, inflammation, and allergic diseases.

Other pharmaceutical compositions disclosed herein are used in methods of treatment and prophylaxis of non-neurological diseases. Examples of such diseases amenable to treatment are cancer (e.g., tumors of non-CNS tissue), inflammation, and allergic diseases.

In prophylactic applications, pharmaceutical compositions are administered to a patient susceptible to, or otherwise at risk of, a disease in an amount and frequency sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, pharmaceutical compositions are administered to a patient suspected of, or already suffering from such a disease in an amount and frequency sufficient to cure, or at least partially arrest, the symptoms of the disease (biochemical, histologic and/or behavioral), including its complications and intermediate pathological phenotypes in development of the disease. An amount of pharmaceutical composition sufficient to achieve at least one of the above objects is referred to as an effective amount, and a combination of amount and frequency sufficient to achieve at least one of the above objects is referred to as an effective regime.

X. Methods of Imaging

As discussed above, the invention provides conjugates comprising a conjugate moiety, which is a substrate of MCT1, linked to an imaging component, as well as agents that are substrates for MCT1 and have an inherent imaging activity. Optionally, the agents also have inherent affinity for a particular antigen or cell type found in the CNS, or the conjugate is provided with an additional conjugate moiety having such affinity. The additional moiety is referred to as a targeting moiety. The targeting moiety can be an antibody or fragment thereof, or any other molecule that specifically binds to a desired antigen or cell type within the brain. The invention further provides pharmaceutical compositions comprising all of these entities. These pharmaceutical compositions can be used for in vivo imaging. The compositions are administered to a patient and preferentially taken up by central nervous system cells after being actively transported from the blood into the brain by brain microvessel endothelial cells expressing MCT1 in the patient. The imaging activity is then detected. In some methods, the imaging component is also a cytotoxic agent. For example many radioisotopes are suitable for both imaging and tumor cytotoxic activity. In such cases, methods of imaging and methods of treatment can be combined. Currently used diagnostic imaging techniques include positron emission tomography (PET), magnetic resonance imaging (MRI), and computed tomography (CT). Actively transported imaging components provide information about, for example, the presence and/or size of a brain tumor. The cell assay methods provided herein can also be used to identify imaging compounds for use outside the CNS, wherein such imaging agents exert undesirable side effect on the CNS.

As can be appreciated from the disclosure above, the present invention has a wide variety of applications. For example, the MCT1 transporter can be used to identify an agent or conjugate that is a substrate for the transporter and that can cross the blood brain barrier and can therefore treat the CNS. The MCT1 transporter also can be used to increase the capacity of an agent to cross the blood brain barrier by identifying a conjugate moiety that is a substrate for the MCT1 transporter and linking the conjugate moiety to the agent. Accordingly, the following examples are offered by way of illustration, not by way of limitation.

EXAMPLES

Example 1

Quantitative PCR Detection of MCT1 Expression in Brain Endothelial Cells

Quantitative PCR was performed to analyze MCT1 expression in human, mouse and rat brain endothelial cells. Endothelial cells from mouse and rat brains were isolated as follows: To isolate an adequate number of brain endothelial cells, brains were removed from 10 adult rats or 20 adult mice. The brains were washed in 70% ethanol, and placed in sterile phosphate buffered saline. Meninges and surface vessels were removed. Cortical gray matter was minced, placed in preparation medium (1 g/L glucose, 25 mM HEPES, 100 U/ml penicillin, 100 µg/ml streptomycin, 10 µg/ml DNAse I, 1 mg/ml collagenase/dispase, in DMEM, adjusted to a pH of 7.4) and incubated for 1 hour at 37° C. Samples were centrifuged for 10 minutes at 1000 ×g. Fat, cell debris, and myelin were discarded. The pellet was resuspended in fresh preparation medium and incubated for an additional 3 hours at 37° C. in a shaking bath. Medium was filtered through a 230 µM nylon sieve followed by a 150 µM nylon sieve. Microvessels were collected by retention on a 60 µM nylon sieve. Capillaries were washed with preparation medium, and then pelleted for RNA isolation.

Human brain tissue was obtained from epileptic foci surgically removed from human patients. Human brain microvessel endothelial cells were isolated essentially as described above.

Total RNA was isolated from the brain endothelial cells using the standard protocol for the RNEasy RNA Isolation Kit (Qiagen). Cells were resuspended in RLT lysis buffer at 10 mls per 0.4 grams of cells. Lysates were vortexed and run through a QiaShredder Column (Qiagen) prior to RNA isolation. Once isolated, the RNA was quantified, run on a 1% agarose gel to ensure integrity, and then stored at −80° C.

Prior to cDNA synthesis, total RNA was DNAse I treated to destroy genomic DNA contamination (Invitrogen DNAseI Kit). Twenty microliters of oligo dT primed single-stranded cDNA was then synthesized from 1 µg total RNA (Invitrogen Thermoscript cDNA Synthesis Kit). The cDNA was treated with RNAse H and stored at −20° C.

Quantitative PCR was performed in a 96-well format using the MJ Research DNA Engine Opticon. For each transporter, a pair of 26 base oligonucleotide primers were used to amplify the specific transporter. Primers were designed to recognize the non-conserved 3' ends of MCT transporter mRNA. The single stranded cDNA was used as a template for a PCR reaction containing human, mouse or rat primers and SYBR Green master mix (Applied Biosystems). Fluorescent signal was read and graphed each cycle. A CT value, or cycle threshold value, was determined for each reaction. This value was defined as the point at which the fluorescent signal of the reaction exceeds background fluorescence. Background fluorescence was calculated as 20 standard deviations above the average signal from cycles 3 through 10. Transcript abundance was normalized to GAPDH. Averaged results from several experiments in which rat MCT family transporters with similar substrate specificity were amplified are shown below in Table 2. The units of measurement are MRNA transcripts detected, per PCR reaction. Results from two mouse MCT1 amplification experiments are shown below in Table 3. Averaged results from 2 human MCT1 amplification experiments are shown below in Table 4.

TABLE 2

MCT family mRNA Expression in Rat Capillary Endothelial Cells

| Gene | transcripts | forward primer | reverse primer |
|---|---|---|---|
| MCT1 | 24,545 | tgccactgaattgataccttgctcc (SEQ ID NO: 2) | tgctcatggccctgggtcaatcctaa (SEQ ID NO: 3) |
| MCT2 | 205 | gcaacaaaagatcgcaaacagtaacg (SEQ ID NO: 4) | tccgacgaaaaatgaaccttgaagag (SEQ ID NO: 5) |
| MCT3 | 509 | agccccacagttaccagccgcctata (SEQ ID NO: 6) | ggctgaagttgggggtaggatggtgg (SEQ ID NO: 7) |

TABLE 2-continued

MCT family mRNA Expression in Rat Capillary Endothelial Cells

| Gene | transcripts | forward primer | reverse primer |
|---|---|---|---|
| MCT4 | 2,285 | aagccccacagttaccagccgcctat (SEQ ID NO: 8) | tggcaatataggagactggggctgaa (SEQ ID NO: 9) |
| MCT5 | 1,897 | tgctgggatggctgttctttctggac (SEQ ID NO: 10) | tgccagagaaatagaaagagcccacg (SEQ ID NO: 11) |
| MCT6 | 8 | ctttggccctaggacagacacacttc (SEQ ID NO: 12) | actcgctcatccacctcttccttacg (SEQ ID NO: 13) |
| MCT7 | 1,774 | attcgaaggtgtggtctagtggttgg (SEQ ID NO: 14) | ggaaatggatcttgggaaatgtgagc (SEQ ID NO: 15) |
| MCT8 | 211 | gccgccttcttgttgtctatcgtggg (SEQ ID NO: 16) | ggccaggctgaagagataggggacgt (SEQ ID NO: 17) |
| MCT9 | 2,409 | aaggcgatgtcataggtctgggtcca (SEQ ID NO: 18) | cttcccgtatgtgaccacgaagactg (SEQ ID NO: 19) |
| MCT10 | 508 | aggggggcttttatcaatgtgtgctcc (SEQ ID NO: 20) | ccccagaaccagaggaggaggcagtg (SEQ ID NO: 21) |
| MCT11 | 459 | tcccgtaggcagcaatcaggtgtttc (SEQ ID NO: 22) | gtggggtgtttctggcgactggagta (SEQ ID NO: 23) |

TABLE 3

MCT1 mRNA Expression in Mouse Capillary Endothelial Cells

| Mouse MCT1 | transcripts | forward primer | reverse primer |
|---|---|---|---|
| Exp. #1 | 30,083 | aggggctctgaggtgttggttcttag (SEQ ID NO: 24) | caaaagcacatccattcagtcggtac (SEQ ID NO: 25) |
| Exp. #2 | 19,007 | aggggctctgaggtgttggttcttag (SEQ ID NO: 24) | caaaagcacatccattcagtcggtac (SEQ ID NO: 25) |
| Exp. #2 | 16,347 | aggggctctgaggtgttggttcttag (SEQ ID NO: 24) | caaaagcacatccattcagtcggtac (SEQ ID NO: 25) |

TABLE 4

MCT1 mRNA Expression in Human Capillary Endothelial Cells

| Human MCT1 | transcripts | forward primer | reverse primer |
|---|---|---|---|
| Exp. | 169,370 | tgggcatgtggcgtcgtcctaattat (SEQ ID NO: 26) | ttcctcctccttgggccctccttctg (SEQ ID NO: 27) |

The enrichment of MCT1 transcripts in brain capillary endothelial cells (BMECs) relative to total brain transcripts was also determined by quantitative PCR as described above. Total RNA was isolated from whole brain samples. MCT1 transcript levels were normalized to GLUT1 transcript levels. GLUT1 transcript levels were determined using the human, mouse and rat GLUT1 primers described in Table 7 below. Table 5 below shows the average MCT1 transcript levels, normalized transcript levels, and ratio of MCT1 transcripts in BMEC versus brain in human, mouse and rat brain.

To confirm the purity of the brain endothelial cell RNA preparations, samples of RNA from each preparation were tested by quantitative PCR for mRNA transcript levels of capillary (GLUT1), neuronal (BNPI) and glial (GFAP) cell markers. The quantitative PCR analysis was conducted as described above. The primers used are shown in Table 6 below. The results of the control gene transcript quantitation are shown in Table 7 below.

TABLE 6

Primers for Quantitative Analysis of Control Genes

| Gene | forward primer | reverse primer |
|---|---|---|
| Human GLUT1 | ggggcatgattggctccttctctgtg (SEQ ID NO: 28) | aggccgcagtacacaccgatgatgaa (SEQ ID NO: 29) |
| Mouse GLUT1 | cgcccattcctgtctcttcctaccca (SEQ ID NO: 30) | tcatggtgtttgtgtggccctcagtg (SEQ ID NO: 31) |
| Rat GLUT1 | gaaccacagggaaagcaactctaatc (SEQ ID NO: 32) | tcgggtcattattttcacgtttcca (SEQ ID NO: 33) |

TABLE 5

MCT1 mRNA Expression in Human, Mouse and Rat Brain Microvessel Endothelial Cells

|  | Average BMEC | | | BMEC % GLUT1 | | | BMEC:Brain Ratio | | |
|---|---|---|---|---|---|---|---|---|---|
|  | Human | Mouse | Rat | Human | Mouse | Rat | Human | Mouse | Rat |
| MCT1 | 169,370 | 16,347 | 24,545 | 21.1 | 9.6 | 18.1 | 13.9 | 3.2 | 3.0 |
| GLUT1 | 802,859 | 169,616 | 135,976 | 100 | 100 | 100 | 43.1 | 3.1 | 9.2 |

TABLE 6-continued

Primers for Quantitative Analysis of Control Genes

| Gene | forward primer | reverse primer |
|---|---|---|
| Human BNPI | cacccccgctttcctttatctccag (SEQ ID NO: 34) | ctgctggtaggggagatgtgaagtgg (SEQ ID NO: 35) |
| Mouse BNPI | acggggggacatcactcagaattacat (SEQ ID NO: 36) | ttcttccttttctcccagccgttag (SEQ ID NO: 37) |
| Rat BNPI | gccacacacagcacagttcagcctcc (SEQ ID NO: 38) | ggacagcactgggcacaagggaagac (SEQ ID NO: 39) |
| Mouse GFAP | aggaaattgctggagggcgaagaaaa (SEQ ID NO: 40) | caccatcccgcatctccacagtcttt (SEQ ID NO: 41) |
| Rat GFAP | ggtgggcaggtgaggaagaaatggag (SEQ ID NO: 42) | tagcagaggtgacaagggggggagtg (SEQ ID NO: 43) |

TABLE 7

Control Gene mRNA Transcript Levels

| Control Gene | Source | Control Gene mRNA Transcript Abundance | | |
|---|---|---|---|---|
| | | Human | Rat | Mouse |
| GLUT1 (Capillary marker) | Capillaries | 802859 | 169616 | 135976 |
| | Whole Brain | 11120 | 13546 | 5278 |
| BNPI (Neuronal marker) | Capillaries | 2614 | 5 | 343 |
| | Whole Brain | 222285 | 67705 | 122509 |
| GFAP (Glial marker) | Capillaries | Not determined | 561 | 670 |
| | Whole Brain | Not determined | 68789 | 24032 |

Example 2

Studies of Cloned MCT1 Transporters: Oocyte Expression

To assess transport function of a specific transporter protein, it can be desirable to clone the cDNA and express the protein in cells that have low endogenous transport activity. Human MCT1 was cloned by PCR, fully sequenced, and subcloned into plasmids that can be used for expression in mammalian cells or *Xenopus* oocytes. The co-subunit, CD147, was also cloned and sequenced, but not found to be necessary for functional expression and was not further characterized. Because many cell lines already exhibit high levels of monocarboxylate transport activity, expression in *Xenopus* oocytes can be advantageous due to the low levels of endogenous amino acid transport. For expression in Xenopus oocytes, in vitro MCT1 cRNA was prepared and injected into defoliculated oocytes.

Figure 3:
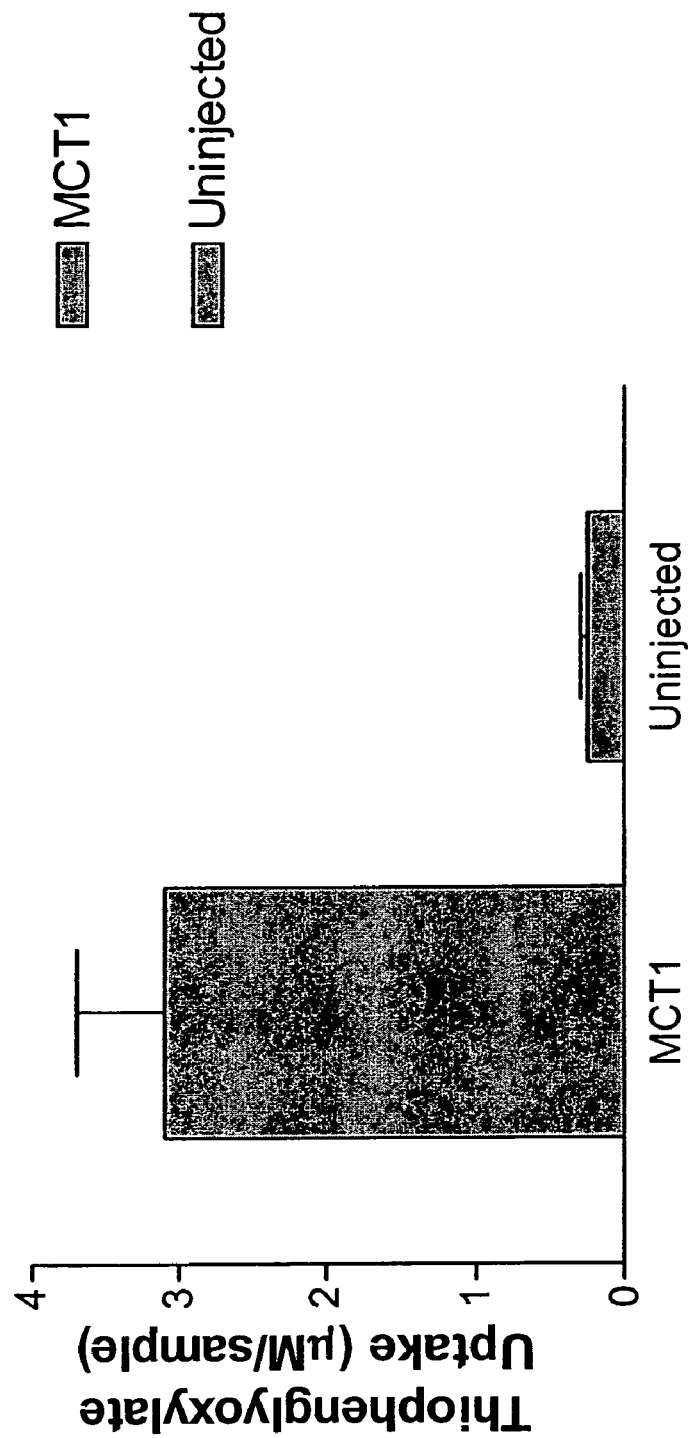
FIG. 3 shows uptake of thiopheneglyoxylic acid (also referred to as 2-thiophene glyoxylate) into oocytes injected with MCT1 cRNA.

Oocytes expressing the MCT1 protein exhibited higher levels of $^{14}$C-lactate uptake than oocytes expressing the MCT4 protein or noninjected control oocytes, as shown in FIG. 2. To measure directly the uptake of possible substrates, an oocyte uptake assay was developed in which compounds are measured by mass spectroscopy. To illustrate this approach, uptake of a metabolically stable MCT1 substrate (2-thiophene glyoxylate) was performed. Oocytes used in this experiment were injected with MCT1 cRNA and incubated at 16-18° C. until maximal transporter expression was reached. Oocytes from the same batch, which were not injected with RNA, were used in the experiment to serve as a control. A 1 mM solution of 2-thiophene glyoxylate was prepared in oocyte ringers (ND96) buffer (90 mM NaCl, 10 mM HemiNa HEPES, 2 mM KCl, 1 MM MgCl$_2$, 1.8 mM CaCl$_2$, pH adjusted to 6.5) containing 0.5% bovine serum albumin. The 2-thiophene glyoxylate was then administered to pools of 8 oocytes for a 4 min duration. Following the incubation, the pools of oocytes were washed 4 times with 0.5% BSA ND96 buffer and separated into 2 oocyte subpools containing 4 oocytes each. Subpools were homogenized in 150 µl of ice cold 80% MeOH/Hg$_2$O, and lysed manually with a P200 pipettor. Lysates were vortexed briefly before being spun in a 4° C. tabletop centrifuge at 13.2 krpm for 15 minutes. Approximately 110 µl of lysate was removed from the eppendorf tubes and placed in a 96-well plate. Lysates were analyzed for 2-thiophene glyoxylate concentrations by liquid chromatography-mass spectroscopy. An example results from these LC-MS-MS compound uptake experiments in oocytes is shown in FIG. 3.

Samples were analyzed by LC-MS-MS as follows. A specific method was developed for each compound, and calibrated against a series of dilutions of known compound concentrations spiked into cellular extract. Typically compound methods were linear over the concentration range 0.1 to 10 mM. Measurements were performed using an API 2000 LC-MS-MS spectrometer equipped with Agilent 1100 binary transporters and a CTC HTS-PAL autosampler. Analyte fragmentation peaks were integrated using Analyst 1.2 quantitation software, and concentrations were calculated using a calibration curve of signals produced by known concentrations of the compound.

Example 3

Studies of Cloned MCT1 Transporters: pH Assay in *Xenopus* oocytes

Figure 5:
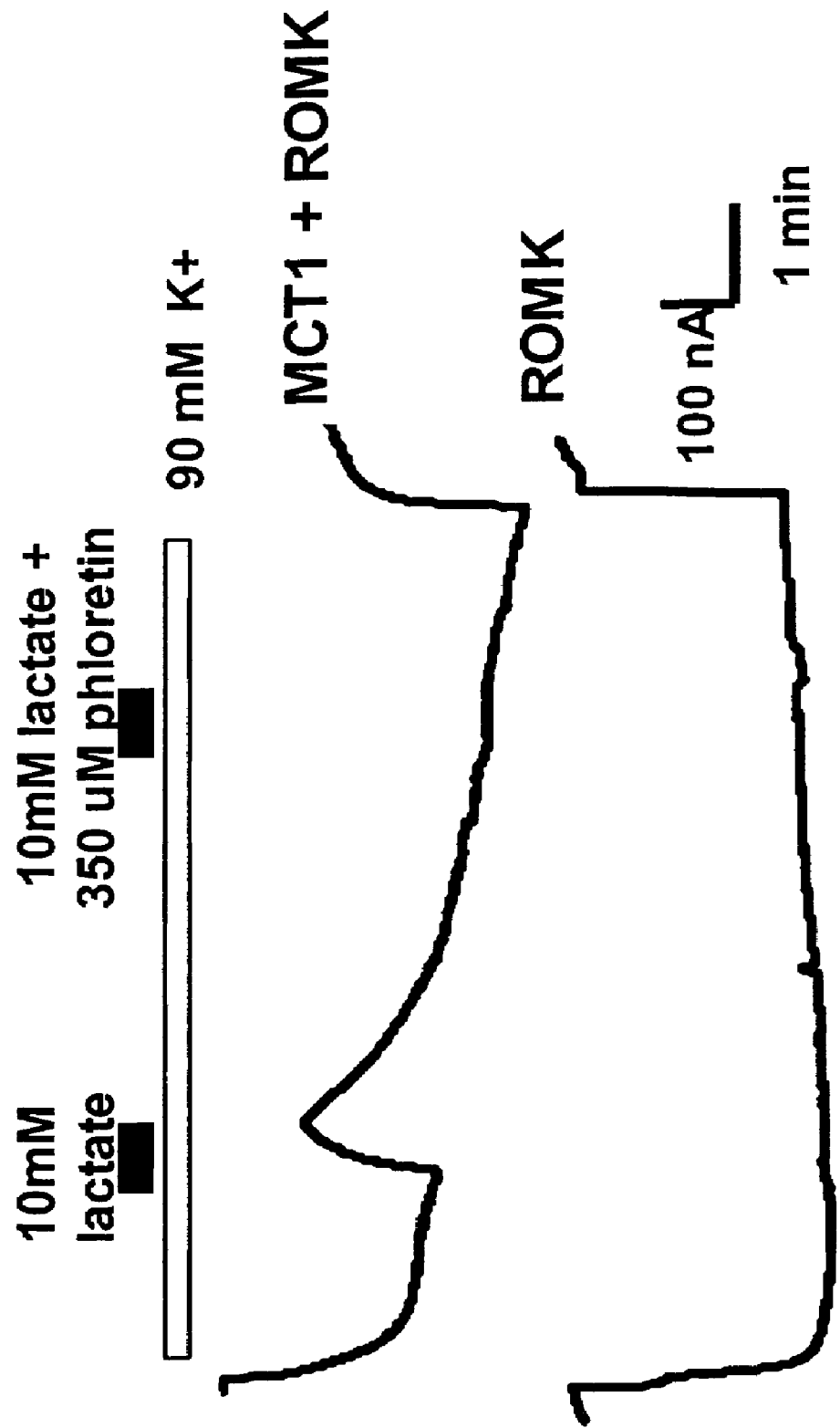
FIG. 5 shows an intracellular pH assay using ROMK and MCT1 injected oocytes for determining substrate uptake.

For more rapid determination of whether a compound is a substrate of the cloned MCT1 transporter, an MCT1 assay in *Xenopus* oocytes that measures intracellular pH using the ROMK potassium channel as a reporter was developed. The assay was performed as follows: MCT1 and MCT4 were co-expressed with ROMK in oocytes by co-injection of cRNA. Transport currents were measured 2-5 days after injection using a two-electrode voltage-clamp (Axon Instruments). All experiments were performed using a modified oocyte Ringers solution (90 mM NaCl, 2 mM KCl, 1.8 mM CaCl$_2$, 1 mM MgCl$_2$, and 10 mM NaHEPES, pH 6.8). For experiments measuring ROMK currents, the above Ringer solution was modified to include 40 mM KCl, The membrane potential of oocytes was held between −30 and −80 mV and current traces were acquired using PowerLab software. ROMK potassium currents were measured by raising the potassium concentration in the perfusion buffer from 2 mM to 40 mM. Application of an MCT1 or MCT4 substrate resulted in intracellular acidification which inhibits ROMK potassium currents, resulting in an outward current. This outward current was not observed in oocytes that were not injected with ROMK or in oocytes injected with ROMK in the absence of extracellular potassium. The specificity of the currents was further determined by co-application of the non-transported MCT1 inhibitor phloretin to block the outward currents. To allow higher throughput application of compounds, the increase in the slope of the outward currents during the first 60 seconds of drug application were measured rather than the differential current induced by addition of the MCT1 substrate. An example of results from this assay is shown in FIG. 5. Data are expressed as a percentage of the response to saturating lactate responses (change in the slope).

Example 4

Studies of Cloned MCT1 Transporters: Uptake into Mammalian Cells

Figure 4:
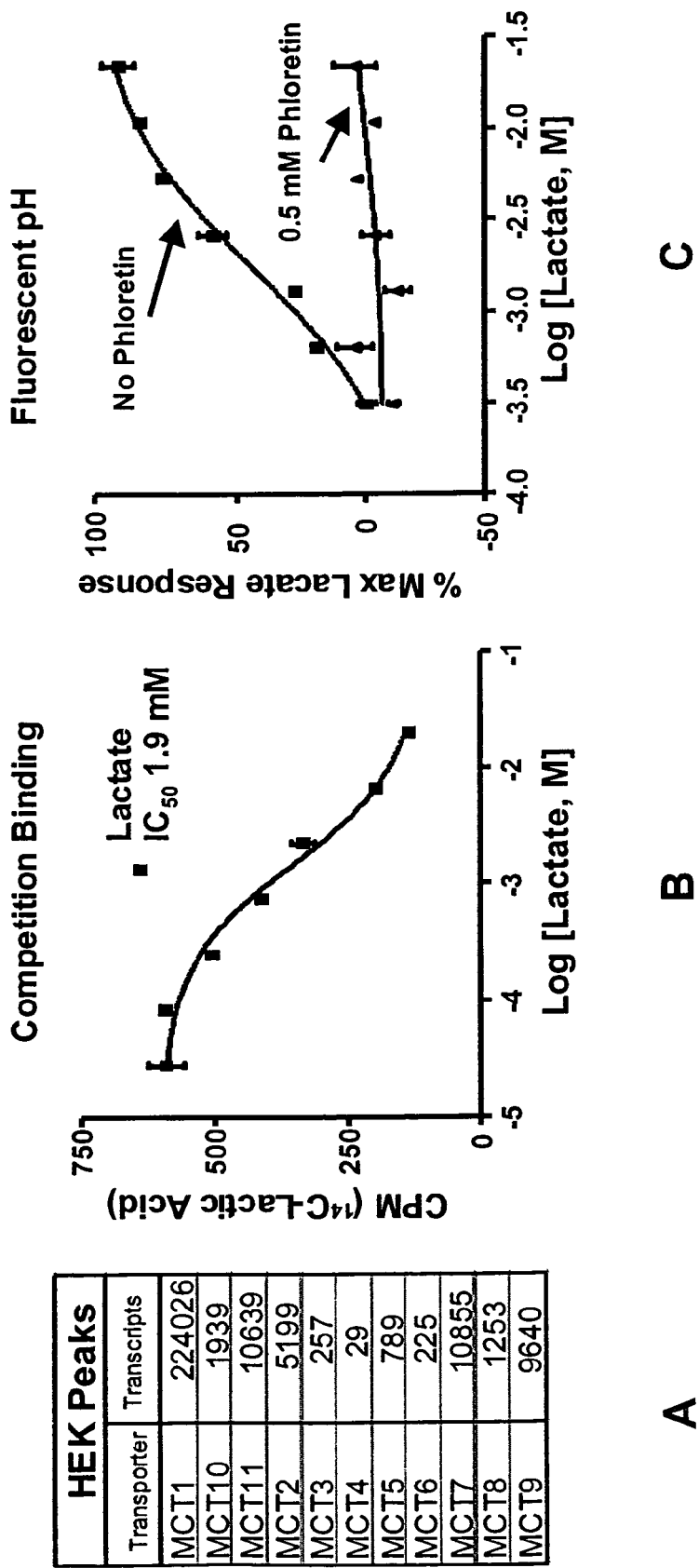
FIG. 4 shows (A) relative expression of MCT transporters in HEK 293 cells, (B) competition binding $^{14}$C-lactic acid by lactate, and (C) a direct uptake assay using HEK-PEAK cells demonstrating lactic acid induced pH changes.

To increase the throughput of MCT1 compound screening, a mammalian cell assay was developed. Because MCT1 mRNA is expressed at detectable levels in human cell lines, over 20 human cell lines were screened for MCT1 expression using quantitative PCR. Cell lines included A498, A549, ASPC, CALU, CAPAN, DLD, DU145, H69AR, HCT8, HEK-PEAK, HELA, HEPG2, HL60, JAR, JUR, KB, LOVO, MCF7, PANC1, PC3, and SW48. The HEK-PEAK cell line was found to have the highest levels of MCT1 mRNA and lacked expression of other transporters for monocarboxylates. HEK-PEAK cells exhibited high levels of $^{14}$C-lactate transport that was not sodium dependent, was activated at low extracellular pH levels, and was inhibited by known MCT1 substrates with affinities similar to cloned human MCT1 protein. An example of lactate transport by LAT1 in HEK-PEAK cells is shown in FIGS. 4B and 4C.

To determine whether a compound interacts with the MCT1 transporter, a competition-binding assay was developed. This assay measures how different concentrations of a test compound block the uptake of a radiolabeled substrate such as lactate. The half-maximal inhibitory concentration ($IC_{50}$) for inhibition of transport of a substrate by a test compound is an indication of the affinity of the test compound for the MCT1 transporter. Competition binding studies were performed as follows. HEK-PEAK cells were plated in 96-well plates at 100,000 cells/well and incubated at 37° C. for 24 hours. Radiolabeled $^{14}$C-lactic acid (~50,000 cpm/well) was added to each well in the presence and absence of various concentrations of unlabeled lactic acid in duplicate or triplicate. Competition experiments were performed in an MES-based saline buffer adjusted to pH 6.8. Plates were incubated at room temperature for 2 minutes. Excess radiolabeled substrate was removed and cells were washed three times with a 96-well plate washer with cold assay buffer. Scintillation fluid was added to each well, the plates were sealed and counted in a 96-well plate-based scintillation counter. Data were graphed and analyzed using non-linear regression analysis with Prism Software (GraphPad, Inc., San Diego, Calif.). Competition binding in HEK-PEAK cells is illustrated in FIG. 4B.

Competition binding studies only demonstrate that a molecule interacts with the MCT1 protein, but do not demonstrate whether the molecule is a substrate and is translocated across the plasma membrane or is non-transported inhibitor or a non-transported ligand. In order to measure whether test compounds are actively translocated across the membrane, and to determine the maximal transport rate, a direct uptake method was developed that utilizes the effect of MCT1 transport on intracellular pH. Since MCT1 is a proton-coupled transporter, uptake of substrate into cells results in an intracellular acidification. To measure intracellular pH responses, HEK-PEAK cells were loaded with the pH-sensitive dye BCECF, and intracellular pH was measured 1-10 minutes after addition of a lactic acid. To demonstrate that the intracellular acidification was due to MCT transport, the test compound was also co-applied with an MCT1 inhibitor, phloretin. An example of lactate responses is shown in FIG. 4C.

Example 5

Efflux Assays

Figure 6:
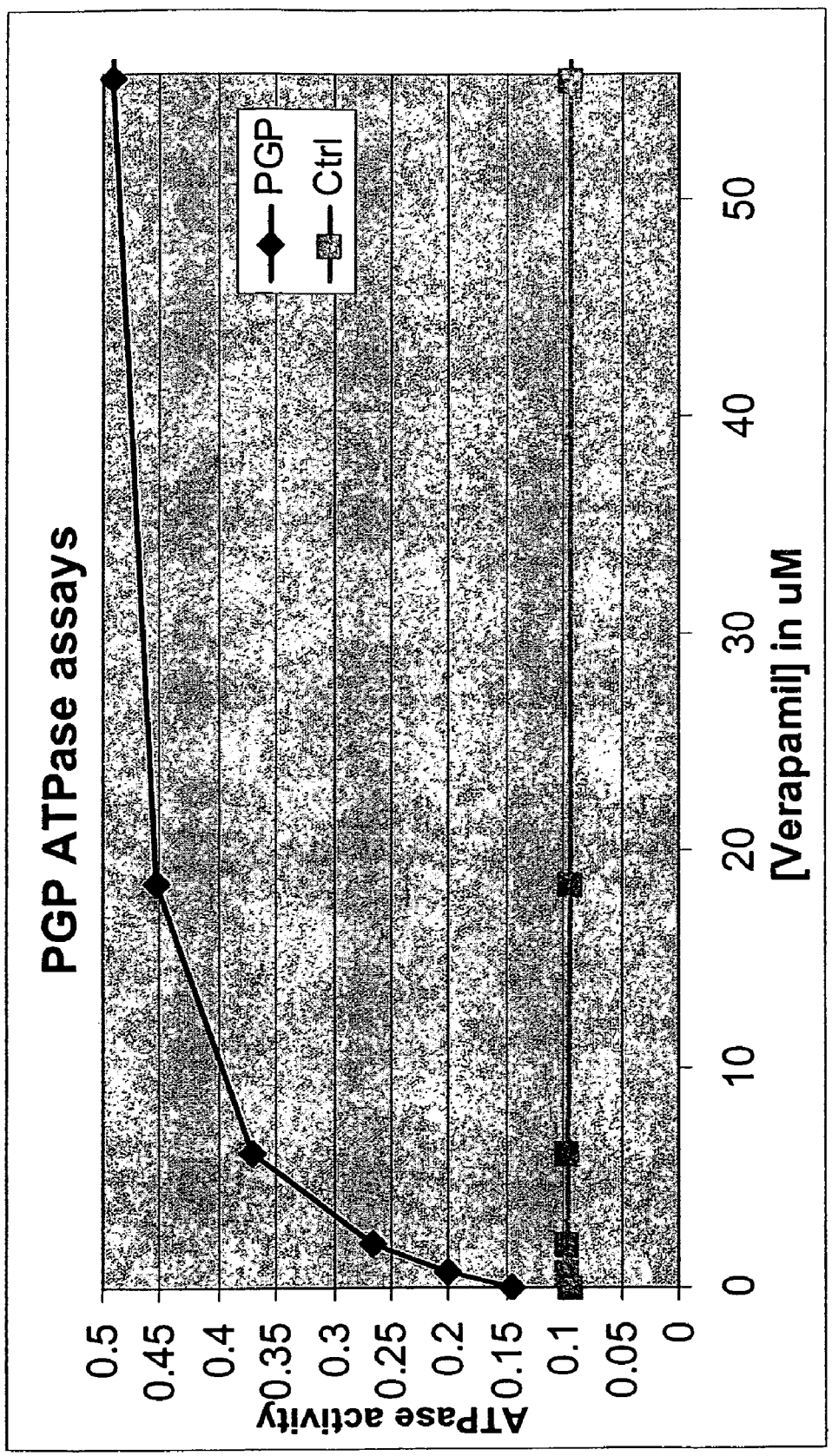
FIG. 6 shows an efflux transporter ATPase activity assay using membrane preparations containing the PgP efflux transporter and the PgP substrate verapamil.

FIG. 6 depicts the results of an efflux experiment in which the PgP substrate verapamil was added to commercial Baculovirus membranes (purchased from BD Biosciences) at various concentrations depicted on the X axis followed by ATPase activity measurement. The ATPase activity measurement was performed using the lactate dehydrogenase/pyruvate kinase coupled enzyme system described by Tietz & Ochoa, Arch. Biochim. Biophys. Acta 78:477 (1958) to follow the decrease in absorbance at 340 nm resulting from the oxidation of NADH, which is proportional to ATPase activity. 5 mM sodium azide ($NaN_3$), 1 mM EGTA, and 0.5 mM Ouabain, each of which inhibit non-specific ATPases in the membranes, were added to the reactions to further enhance the specificity of the PgP ATPase signal. The other components in the assay mixture were 25 mM Tris, pH 7.8, 100 mM NaCl, 10 mM KCl, 5 mM $MgCl_2$, 1 mM DTT, 2 mM phosphoenolpyruvate, 1 mM NADH, 0.1 mg/ml lactate dehydrogenase, 0.1 mg/ml pyruvate kinase, 5 mM ATP, and 6 µg PgP or control membranes. FIG. 6 demonstrates that as the concentration of verapamil was increased, the ATPase activity in PgP-containing membranes but not in control membranes also increased.

Figure 7:
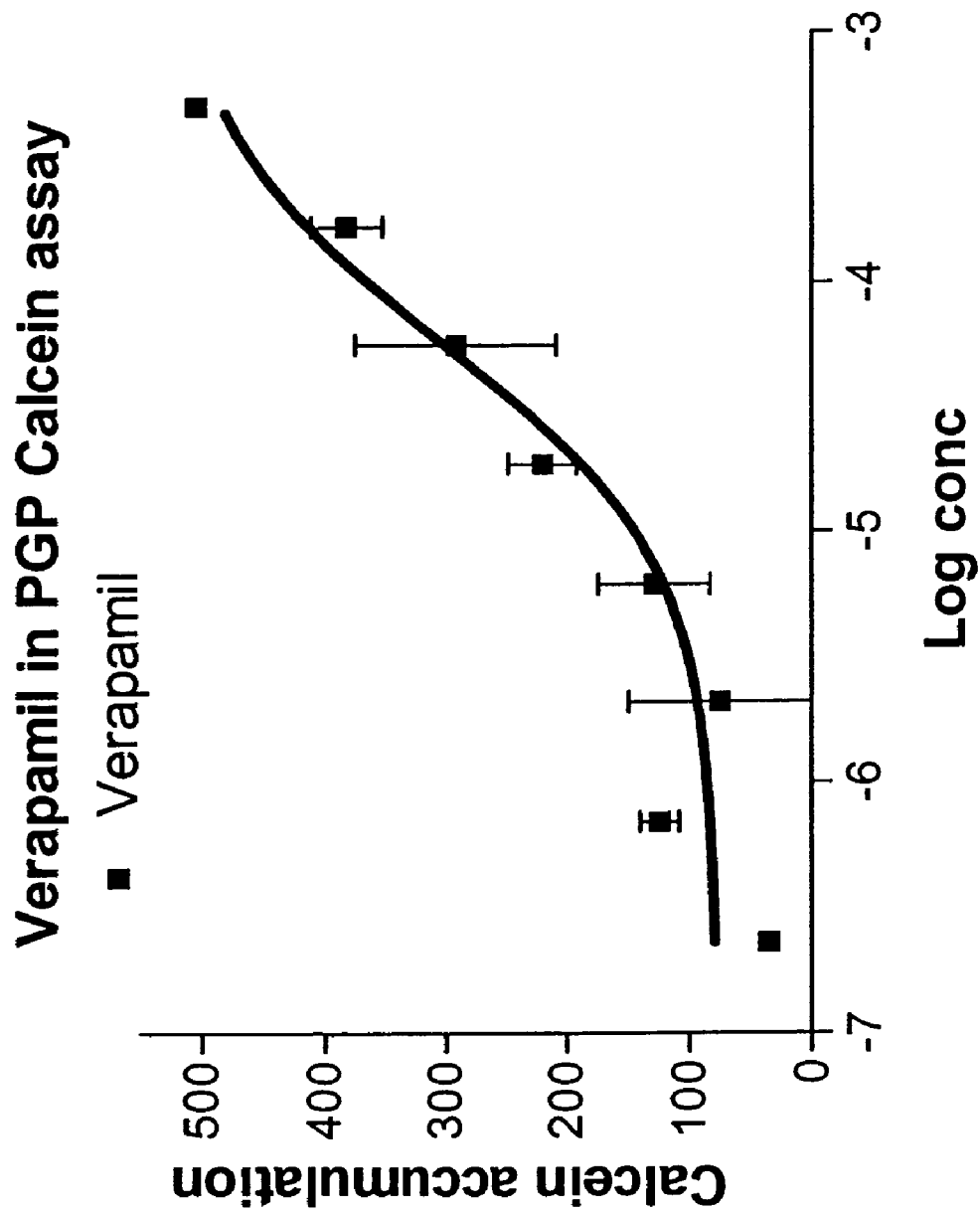
FIG. 7 shows an efflux transporter competition assay using the reporter molecule calcein-AM and the PgP substrate verapamil.

FIG. 7 depicts the results of an efflux competition assay. A tetracycline-inducible PgP expression construct (TREx-PgP, made with TREX plasmid, Invitrogen Inc. Carlsbad, Calif.) was transfected into HEK cells. The cells were incubated with PgP substrate 5 µM calcein-AM, which passively diffuses into the cells, as well as with various concentrations of the PgP substrate verapamil as shown in FIG. 7. As the concentration of PgP substrate verapamil was increased, more calcein-AM accumulated in the cells and was converted to the fluorescent product calcein.

Figure 8:
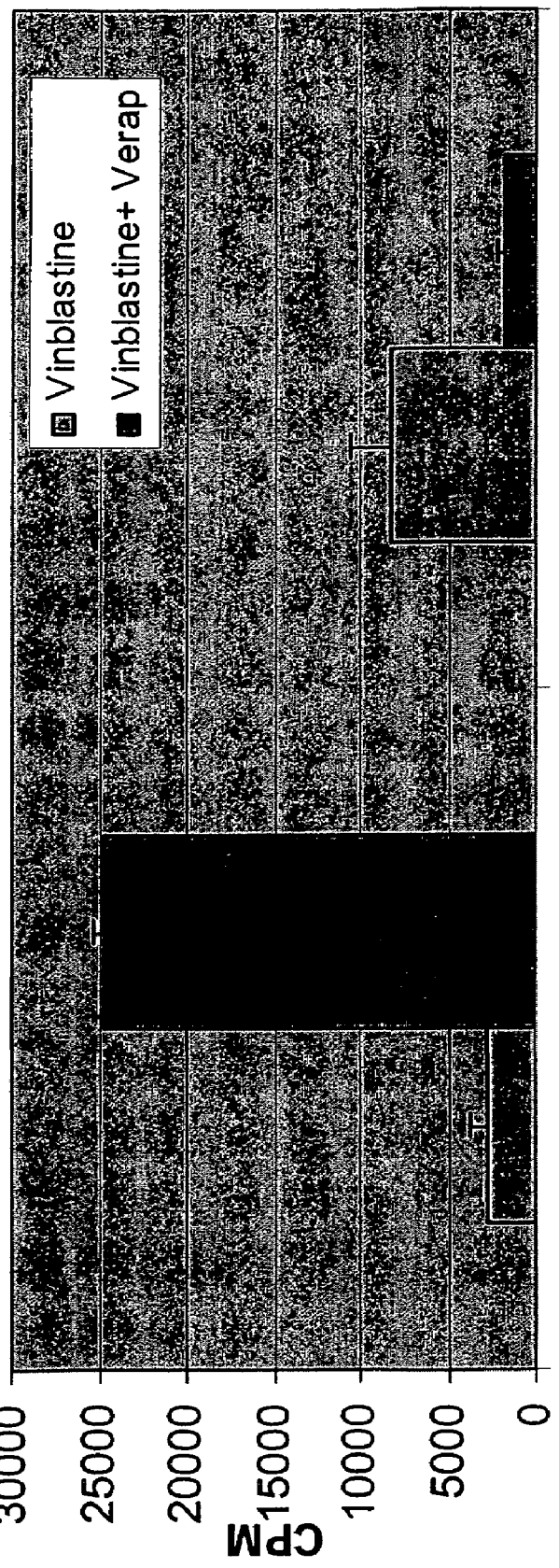
FIG. 8 shows a direct efflux transport assay using a polarized monolayer of MDCK cells transfected with a tetracycline-inducible PgP expression construct.

FIG. 8 depicts the results of a cellular transwell monolayer efflux assay. MDCK cells transfected with the tetracycline-inducible TREx-PgP expression vector were seeded on polycarbonate filter membranes in transwell dishes and grown for 3-5 days, yielding a polarized monolayer with tight junctions between cells. In this example, apical to basolateral and basolateral to apical transport of 2.5 nM (approximately 100,000 cpm) radiolabeled PgP substrate $^3$H-vinblastine was measured in the absence and presence of 250 µM of the inhibitor/competitor verapamil. The left set of bars depicts apical to basolateral transport, while the right set of bars depicts basolateral to apical transport. Apical to basolateral transport of $^3$H-vinblastine was strongly increased and basolateral to apical transport of $^3$H-vinblastine was strongly decreased in the presence of verapamil, indicating that $^3$H-vinblastine is a substrate of PgP.

Example 6

Recombinant MCT1 Expression Assays

Human MCT1 (hMCT1) is expressed at high levels in most mammalian cell lines. hMCT1 is a high capacity transporter, so low levels of hMCT1 expression may result in significant substrate transport. To control the level of hMCT expression, an inducible tet promoter-hMCT1 expression construct was prepared using the Gateway plasmid cloning system following manufacturers instructions (Invitrogen). The tet-MCT1 inducible construct was transfected into HEK-TREx cells using Fugene transfection following manufacturers instructions (Roche Biosciences). When the transfected cells were tested in an uptake assay, the amount of tetracycline-inducible MCT1-mediated transport of $^{14}$C-lactate was about 20% higher than the level of endogenous uptake seen in non-induced cells. The addition of an excess of unlabeled lactate competed with the uptake of $^{14}$C-lactate.

To identify cell lines that had a higher level of induced MCT1 expression, the level of recombinant hMCT1 expression in other cell lines was determined by transient transfection. These cell lines included A549 cells, MDA-MB-231 and two non-human TREx cell lines MDCK-TREx and LLCPK-TREx cell lines. MDCK and LLCPK host TRex cell lines were prepared following manufacturers protocol with several modifications (Invitrogen). Cells were transfected using Amaxa Transfection agent, and single cell clones were obtained by FACS. The presence of the tetracycline inducible promoter was verified by transfection with a tetracycline-inducible luciferase plasmid. The final clone was selected for high levels of tetracycline induced luciferase expression and formation of single cell monolayers when cultured on transwell filters. These host cell lines were transfected with a hMCT1 cDNA or a control plasmid lacking the hMCT1 gene. The construct was transfected into the host cells using an Amaxa nucleoporator following the manufacturer's instructions.

Figure 9:
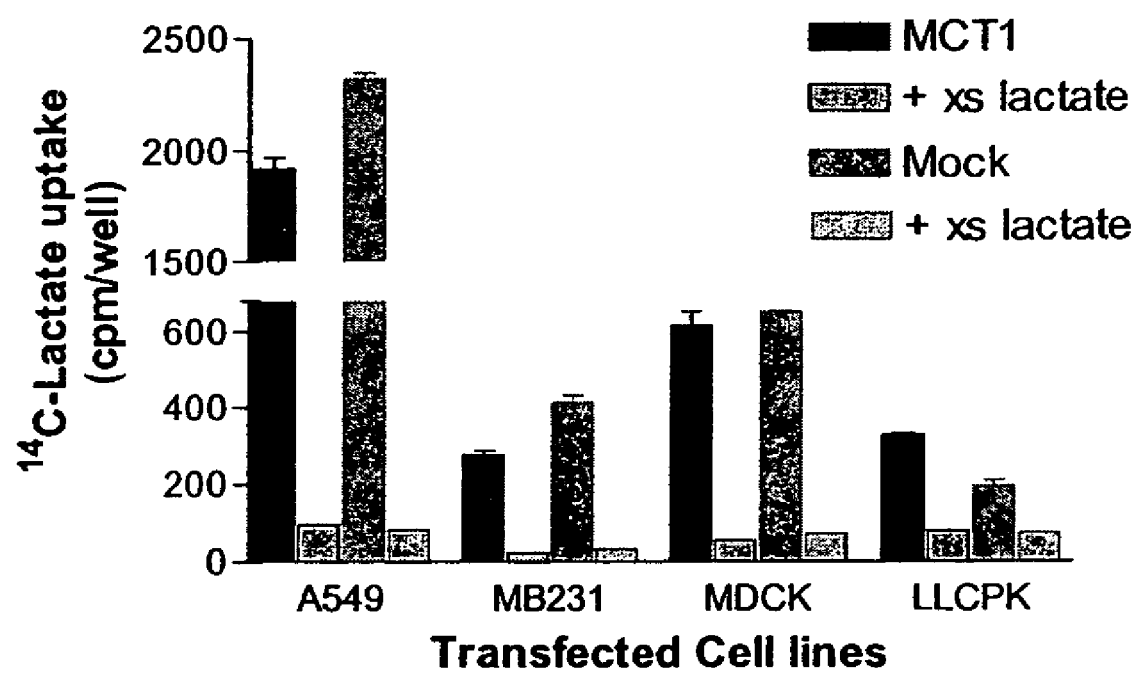
FIG. 9 shows a $^{14}$C-lactate uptake assay for cells transfected with hMCT1 cDNA or a control plasmid (mock). Endogenous MCT1 activity in each cell was assessed by measuring uptake in the presence and absence of excess unlabeled lactate ("xs lactate").

FIG. 9 depicts the results of the $^{14}$C-lactate transport assays on the transfected host cells. A549, MDA-MB-231 and MDCK-TREx host cells exhibited lower $^{14}$C-lactate uptake after transient transfection with hMCT1 cDNA than mock transfected cells. For the LLCPK-TREx cell line, the background endogenous MCT1 activity was low, and there was a detectable increase in $^{14}$C-lactate uptake upon hMCT1 expression. Therefore, the LLCPK-TREx cell line was chosen as the host cell line for recombinant expression of hMCT1.

To develop both inducible and constitutive LLCPK-TREx cell lines, hMCT1 cDNA was subcloned into both an inducible (pTREx) and a constitutive (pMO) plasmid to make plasmids pTREx-hMCT1 and pMO-hMCT1, respectively. Plasmids pTREx-hMCT1 and pMO-hMCT1 were transfected into LLCPK-TREx cell lines and transfectants selected for G418-resistance.

FIG. 10 depicts the results of an uptake experiment showing inducible uptake of (A) $^{14}$C-lactate and (B) thiopheneglyoxylic acid by the LLCPK-TREx cell line containing plasmid pTREx-hMCT1. Uptake of $^{14}$C-lactate was measured as follows: radiolabeled $^{14}$C-lactic acid (~50,000 cpm/well) was added to each well in triplicate. Experiments were performed in an MES-based saline buffer adjusted to pH 6.8. Plates were incubated at room temperature for 2 minutes. Excess radiolabeled substrate was removed and cells were washed three times with a 96-well plate washer with cold assay buffer. Scintillation fluid was added to each well, the plates were sealed and counted in a 96-well plate-based scintillation counter. Uptake of thiopheneglyoxylic acid was measured similarly to $^{14}$C-lactate, except cells were washed and compound extracted with a 50% ethanol solution. Levels of extracted thiopheneglyoxylate were measured using mass spectroscopy as described above. Negative control values were determined by measuring the uptake into non-tet treated (un-induced) or parental LLCPK (constitutive) cells. The transfected LLCPK-TREx cells show a significant increase in MCT1 substrate uptake upon induction with tetracycline.

MCT1 has been described in the literature as requiring a cofactor, CD147, for optimal expression. To determine whether co-expression of CD147 would increase MCT1-mediated transport, a DNA construct encoding a hMCT1-rCD147 fusion protein was prepared (SEQ ID NO:44 and SEQ NO:45, respectively The hMCT1-rCD147 DNA construct was subcloned into both the inducible (pTREx) and constitutive (pMO) plasmids to make plasmids pTREx-hMC1-rCD147 and pMO-hMCT1-rCD147, respectively. Plasmids pTREx-hMC1-rCD147 and pMO-hMCT1-rCD147 were transfected into the LLCPK-TREx cells and transfectants selected for G418-resistance.

To further analyze cells expressing the hMCT1-rCD147 fusion protein, a commercially available antibody to rCD147 (Research Diagnostics, Inc.) was used to FACS-sort the cells. Upon tet-induction, the cells formed two groups, low-expressing clones group and high-expressing clones. The high expressing clones were collected.

Figure 11:
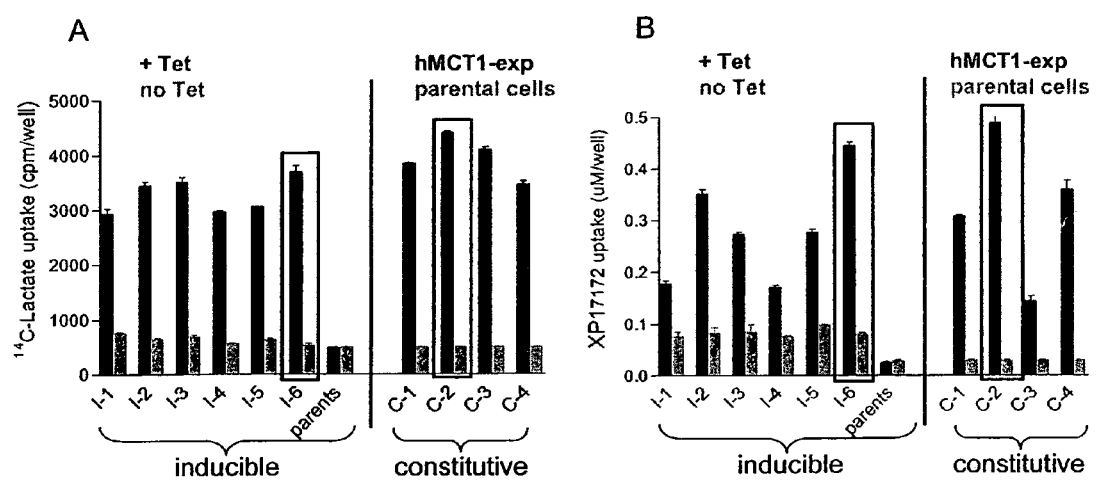
FIG. 11 shows the screening of recombinant clonal LLCPK cell lines for the expression levels of hMCT1-rCD147 fusion protein. Uptake of (A) $^{14}$C-lactate or (B) 2-thiopheneglyoxylic acid into various tet-inducible (I1-6) or constitutive (C1-4) cell lines is shown. Negative control values were determined by measuring the uptake into non-tet treated (un-induced) or parental LLCPK (constitutive) cells.
Figure 12:
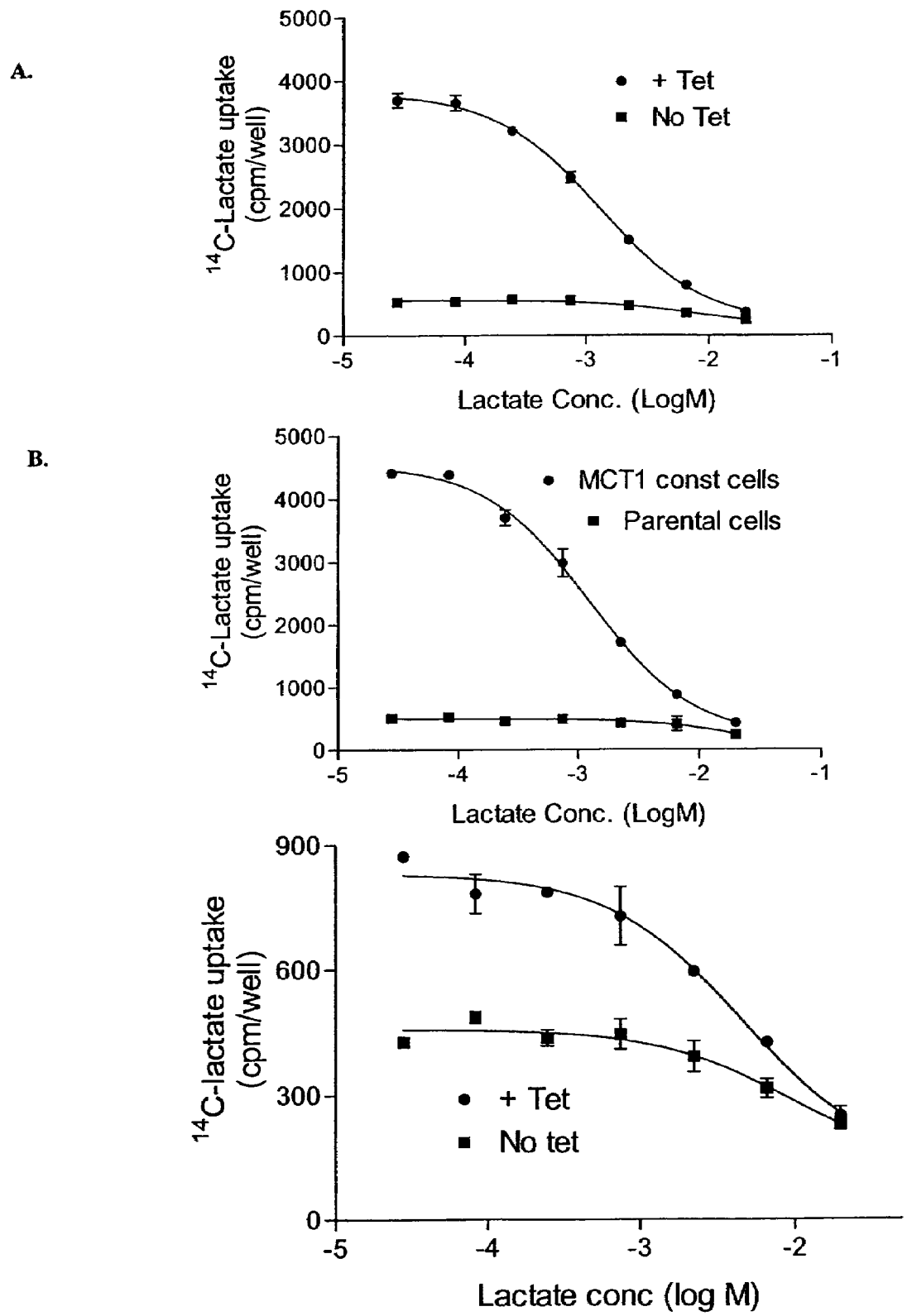
FIG. 12 shows a comparison of $^{14}$C-lactate uptake at different lactate concentrations by (A) a tet-inducible hMCT1-rCD147-expressing cell line, (B) a constitutive hMCT1-rCD147-expressing cell line, and (C) a tet-hMCT1-expressing cell line. Negative control values were determined by measuring the uptake into non-tet treated (un-induced) or parental LLCPK (constitutive) cells.

FIG. 11 shows the results of the analysis of the high-CD 147 expressing cells in uptake assays with radiolabeled lactate or with an MCT substrate, 2-thiopheneglyoxylic acid. Uptake of (A) $^{14}$C-lactate or (B) 2-thiopheneglyoxylic acid into various tet-inducible (I1-6) or constitutive (C1-4) cell lines is shown. Negative control values were determined by measuring the uptake into non-tet treated (un-induced) or parental LLCPK (constitutive) cells. By this assay both an inducible (I-6) and a constitutive (C-2) cell line expressing the hMCT1-rCD147 fusion protein were identified that exhibited significant increases in hMCT1-rCD147 expression as compared with the control cells. FIG. 12 shows a comparison of the uptake of $^{14}$C-lactate at varying concentrations of lactate by (A) inducible and (B) constitutive hMCT1-rCD147 cell lines. FIG. 11 also shows the uptake of $^{14}$C-lactate at varying concentrations of lactate by (C) inducible hMCT1 cell lines.

To confirm the pharmacology of the hMCT1-rCD147 fusion proteins was the same as that of the unmodified version of hMCT1, the hMCT1-rCD147-expressing cells lines were tested in a competitive binding and uptake assay. Eight different MCT1 substrates were tested for their ability to inhibit the uptake of $^{14}$C-lactate into isolated cell lines inducibly or constitutively expressing hMCT1-rCD147 fusion protein and into cells endogenously expressing hMCT1.

Referring to FIG. 13, the rank order of the potencies of the eight tested compounds was generally the same in the three cell types. Compounds 2 (L-alpha-hydroxy-isocaproic acid), 4 (2-thiopeneglyoxylate), 5 (benzoic acid), 6 (lactic acid), 7 (nicotinic acid) and 8 (phenylacetic acid) exhibited higher affinity for the MCT1-rCD147 fusion protein than hMCT1 alone.

Example 7

Study of α-Hydroxybutyrate Transport

Figure 14:
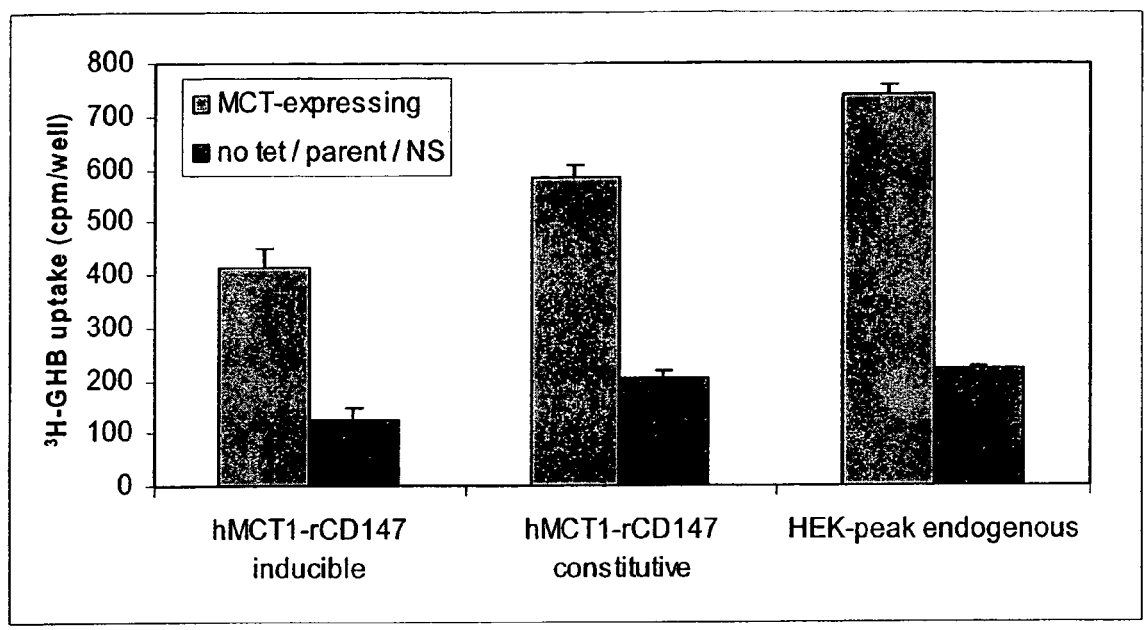
FIG. 14 shows a transport assay with a tet-inducible hMCT1-rCD147-expressing cell line, a constitutively expressing hMCT1-rCD147-cell line, and a tet-hMCT1-expressing cell line. Uptake of tritiated α-hydroxybutyrte (GHB) was increased in cell lines overexpressing MCT1. Negative control values were determined by measuring the uptake into non-tet treated (un-induced) or parental LLCPK (constitutive) cells.

To determine whether α-hydroxybutyrate (GHB) is a substrate for MCT1, an uptake assay was performed using tritiated α-hydroxybutyrate. A recent publication suggested GHB accumulation in the rat brain is inhibited by known MCT substrates. (Bhattacharya & Boje, JPET 311:92-94 (2004).) FIG. 14 shows the results of the uptake study. Cells inducibly or constitutively expressing hMCT1-rCD147 fusion protein exhibited increased uptake of labeled GHB, as compared with uninduced or control cells. Cells over expressing MCT1 protein also exhibited increased uptake of labeled GHB, as compared with control cells.

Example 8

Localization of MCT1 in the Human Brain

An anti-MCT1 antibody was used to stain sections of human brain using tissue slides from Lifespan Technologies. To develop antibodies against MCT1, we synthesized a GST-fusion (glutathion-S-transferase-fusion) proteins using peptides from the C-terminus of MCT1. The GST-fusion protein was comprised of the glutathion-S-transferase protein bound to a 55 amino acid chain portion of the MCT1 transporter (the 55 amino acids from the C-terminus of MCT1 with the sequence RLLAKEQKANEQKKESKEEET-SIDVAGKP-NEVTKTAESPDQKDTEGGPKEEESPV; SEQ ID NO:46. The purified GST-fusion proteins were each injected in rabbits. Specific antibodies were affinity purified from rabbit sera using a column coated with the fusion protein. Paraffin-embedded human brain sections were deblocked, heat treated for antigen retrieval, and stained with the MCT1 antibody and an alkaline-phosphatase conjugated goat anti-rabbit antibody (Jackson Labs). Staining was detected by the DAB colorometric method. The brain sections showed vessel staining in the cerebellum and cerebral cortex and strong basolateral staining in the choroid plexus epithelium.

Although the foregoing compounds, conjugates and methods have been described in detail for purposes of clarity of understanding, it will be obvious that certain modifications may be practiced within the scope of the claim(s) granted herefrom. Unless otherwise apparent from the context, any element, embodiment, or step can be used in combination with any other. All publications and patent documents cited herein are hereby incorporated by reference in their entirety for all purposes to the same extent as if each were so individually denoted.

The invention claimed is:

1. A method of screening an agent, conjugate or conjugate moiety for capacity to be transported through the blood brain barrier, comprising:
   (a) providing a cell expressing the MCT1 transporter, wherein:
   a nucleic acid molecule encoding the MCT1 transporter has been transfected or injected into the cell; and
   the MCT1 transporter is the protein encoded by SEQ ID NO: 1 or has at least 90% sequence identity to the protein encoded by SEQ ID NO:1, and the MCT1 transporter can transport lactic acid, the MCT1 transporter being situated in the plasma membrane of the cell;
   (b) contacting the cell with an agent, conjugate or conjugate moiety in vitro; and
   (c) determining whether the agent, conjugate or conjugate moiety passes through the plasma membrane via the MCT1 transporter, passage through the plasma membrane via the MCT1 transporter indicating the agent, conjugate or conjugate moiety has capacity to be transported through the blood brain barrier;
   wherein:
   if step (b) comprises contacting the cell with the agent, the agent is a neuropharmaceutical agent or an imaging component;
   if step (b) comprises contacting the cell with the conjugate, the conjugate comprises an agent that is a neuropharmaceutical agent or an imaging component; or
   if step (b) comprises contacting the cell with the conjugate moiety, the method further comprises linking the conjugate moiety to an agent that is a neuropharmaceutical agent or an imaging component, and
   provided if the agent is a cytotoxic agent or an imaging component, the method further comprises:
   (i) administering the agent, conjugate, or conjugate moiety to a peripheral tissue of an animal and measuring the amount of agent, conjugate, or conjugate moiety that passes through the blood brain barrier into the brain of the animal; or (ii) contacting the agent to one side of a polarized monolayer of brain microvessel endothelial cells; and determining whether the agent is transported across the polarized monolayer, wherein if the agent is transported across the polarized monolayer it has the capacity to be transported through the blood brain barrier.

2. The method of claim 1, wherein the cell is an oocyte.

3. The method of claim 1, wherein the cell is a human embryonic kidney HEK-PEAK cell.

4. The method of claim 1, wherein the determining is performed by a competition assay.

5. The method of claim 1, wherein the determining is performed by a direct uptake assay.

6. The method of claim 1, wherein the determining is performed by a pH assay.

7. The method of claim 1, wherein the cell is transformed with an SV40 large T antigen that can be expressed in a temperature sensitive fashion.

8. The method of claim 1, wherein the agent is other than a chemotherapeutic agent or imaging component.

9. The method of claim 1, wherein the determining step determines that the agent, conjugate or conjugate moiety passes through the plasma membrane via the MCT1 transporter; and the method further comprises:

(d) modifying the agent, conjugate or conjugate moiety; and (e) determining if the modified agent, conjugate or conjugate moiety is transported with a higher $V_{max}$ by the MCT1 transporter than the agent, conjugate or conjugate moiety.

10. The method of claim 1, wherein the neuropharmaceutical agent is a cytotoxic neuropharmaceutical agent selected from the group consisting of platinum, nitrosourea, nitroimidazole, and nitrogen mustard.

11. The method of claim 1, wherein the agent, conjugate or conjugate moiety comprises a monocarboxylic acid.

12. The method of claim 11, wherein the monocarboxylic acid is selected from the group consisting of lactic acid, pyruvic acid, nicotinic acid, 2-thiophene glyoxylate, pravastatin, butyric acid, salicylic acid, and carindicillin.

13. The method of claim 1, further comprising:

(d) providing a cell expressing at least one efflux transporter;

(e) contacting the cell with the agent, conjugate or conjugate moiety in vitro;

(f) determining that the agent, conjugate or conjugate moiety is transported by the at least one efflux transporter selected from the group consisting of the P-glycoprotein transporter, the multidrug resistance protein transporter, and the breast cancer resistance protein transporter; and determining the efflux transporter activity of the agent, conjugate or conjugate moiety.

14. The method of claim 13, further comprising:

(g) determining the MCT1 transporter activity of the agent, conjugate or conjugate moiety;

(h) modifying the agent, conjugate or conjugate moiety;

(i) establishing that the modified agent, conjugate or conjugate moiety retains MCT1 transporter activity, (j) determining the MCT1 transporter activity of the modified agent, conjugate or conjugate moiety;

(k) determining the efflux transporter activity of the modified agent, conjugate or conjugate moiety; and (l) comparing the ratio of MCT1 transporter activity to the efflux transporter activity for the agent, conjugate or conjugate moiety and the ratio of MCT1 transporter activity to the efflux transporter activity for the modified agent, conjugate or conjugate moiety wherein an increased ratio of MCT1 transporter activity to efflux transporter activity demonstrates that the modification improves the capacity of the agent, conjugate or conjugate moiety to be transported through the blood brain barrier.

15. The method of claim 13 or 14, wherein the efflux transporter activity is determined by conducting an assay selected from the group consisting of:

(a) an efflux transporter ATPase activity assay;

(b) an efflux transporter competition assay; and (c) a direct efflux transport assay across a polarized monolayer of cells.

16. The method of claim 13 or 14, wherein the efflux transporter activity is the $V_{max}$ for the efflux transporter.

17. The method of claim 14, wherein the MCT1 transporter activity is the $V_{max}$ for the MCT1 transporter.

* * * * *

UNITED STATES PATENT AND TRADEMARK OFFICE
CERTIFICATE OF CORRECTION

PATENT NO. : 7,452,680 B2  Page 1 of 1
APPLICATION NO. : 11/026545
DATED : November 18, 2008
INVENTOR(S) : Zerangue It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 484 days Delete the phrase "by 484 days" and insert -- by 808 days --

Signed and Sealed this

Twenty-fifth Day of May, 2010

David J. Kappos
*Director of the United States Patent and Trademark Office*

```
                              SEQUENCE LISTING

<160> NUMBER OF SEQ ID NOS: 46

<210> SEQ ID NO 1
<211> LENGTH: 3410
<212> TYPE: DNA
<213> ORGANISM: Homo sapiens

<400> SEQUENCE: 1
tgcgacgtga ctggctagct gcgtgggtac tggaacaagc aaacgaggca gcgagcgaag      60
gacgggagcc ggaccctggg ccccgtggaa ctccagcctg cgccaccacg tcacgcacac     120
gctcggcgct gcgatccgcg catataacga tatttggatt tgacctgcat tttggaattt     180
atctacactt aaaatgccac cagcagttgg aggtccagtt ggatacaccc ccccagatgg     240
aggctggggc tgggcagtgg taattggagc tttcatttcc atcggcttct cttatgcatt     300
tcccaaatca attactgtct tcttcaaaga gattgaaggt atattccatg ccaccaccag     360
cgaagtgtca tggatatcct ccataatgtt ggctgtcatg tatggtggag gtcctatcag     420
cagtatcctg gtgaataaat atggaagtcg tatagtcatg attgttggtg gctgcttgtc     480
aggctgtggc ttgattgcag cttctttctg taacaccgta cagcaactat acgtctgtat     540
tggagtcatt ggaggtcttg ggcttgcctt caacttgaat ccagctctga ccatgattgg     600
caagtatttc tacaagaggc gaccattggc caacggactg gccatggcag gcagccctgt     660
gttcctctgt actctggccc ccctcaatca ggttttcttc ggtatctttg gatggagagg     720
aagctttcta attcttgggg gcttgctact aaactgctgt gttgctggag ccctcatgcg     780
accaatcggg cccaagccaa ccaaggcagg gaaagataag tctaaagcat cccttgagaa     840
agctggaaaa tctggtgtga aaaaagatct gcatgatgca aatacagatc ttattggaag     900
acaccctaaa caagagaaac gatcagtctt ccaaacaatt aatcagttcc tggacttaac     960
cctattcacc cacagaggct ttttgctata cctctctgga aatgtgatca tgtttttttgg    1020 actctttgca cctttggtgt ttcttagtag ttatgggaag agtcagcatt attctagtga    1080
gaagtctgcc ttccttcttt ccattctggc ttttgttgac atggtagccc gaccatctat    1140
gggacttgta gccaacacaa agccaataag acctcgaatt cagtatttct ttgcggcttc    1200
cgttgttgca aatggagtgt gtcatatgct agcaccttta tccactacct atgttggatt    1260
ctgtgtctat gcgggattct ttggatttgc cttcgggtgg ctcagctccg tattgtttga    1320
aacattgatg gaccttgttg gaccccagag gttctccagc gctgtgggat tggtgaccat    1380
```

```
tgtggaatgc tgtcctgtcc tcctggggcc accacttttta ggtcggctca atgacatgta   1440
tggagactac aaatacacat actgggcatg tggcgtcgtc ctaattattt caggtatcta   1500
tctcttcatt ggcatgggca tcaattatcg acttttggca aaagaacaga aagcaaacga   1560
gcagaaaaag gaaagtaaag aggaagagac cagtatagat gttgctggga agccaaatga   1620
agttaccaaa gcagcagaat ctccggacca gaaagacaca gaaggagggc caaggagga   1680 ggaaagtcca gtctgaatcc atggggctga agggtaaatt gagcagttca tgacccagga   1740
tatctgaaaa tattctactg gcctgtaatc taccagtggt gctcaatgca aatagtagac   1800
atttgtgtgg aaatcatacc agttgttcat tgatgggatt tttgtttgac tccttaccaa   1860
tagcctgaat ttgaggaggg aatgattggt agcaaaggat gggggaaaga agtaggttct   1920
gttttgtttt gttttaatct tagcttttaa tagtgtcata aagattataa tatgtgcctt   1980 aagtttagt cttagaaact ctagagagcc ttaacttctt aaaccatttt tgctgaattc   2040
atctatttcg agtgttgtgt taaaaggaaa aataacaact aacttgtttg aggcaaatct   2100
aaaatttaaa attaatcttg cttcattgtt acatgtaata tatttcagac attttcactg   2160
gaagatttat gaacagaaat attggttgaa agttagagat tttacaaaat gctgacaaaa   2220
atattttcct agcatcagta gatttctggc atatgtttct gctagctata tatttaggaa   2280
attcaaagca taaaactttg gcaacatctt ggctgttcta gacacagtgt acttgtcaac   2340
ccctctcagg tacctttttct tgggatgctt attagaagcc aagtaaagtg cttaaggttt   2400
gttttcatta aattagctat ttctgctccc ctgttcaaag atgcattttg agtgtttata   2460
gatcactgcc ctttttgaaa tcacctggta ttatttttct tactggaaaa gttagtatta   2520
aaatctacag aactacatat ttgtgcctcc ttggtaaata caacacatct aattaaatgt   2580
agacagatat ttcaaacatc agctgaattc acttaagttt ttccaaaacc tcagttaaac   2640
tgtgaagcta ttggaatttt ttttttcctgg aattttttccc ctttgattca cagtggtccc   2700
atttatatct gcttctagct tagtgctatg tgtgagatat gtgtgtgttt ggtgtttttg   2760
tttttttgtt tttttttttt taaggtttgc aaattaaaaa gggccagaaa aatttggcac   2820
caggcaaacg aataaagata ggattgggaa agaagttgct aagtgtgctt agttttaata   2880
agtaattcct tctctttttt cagagaaggc cttacagaaa attgttgtgc ttagaattgc   2940
tggatgcatt tttaccctcc acacaaacct aaaaattttg tgacccctttt cacttacctg   3000 aaaagtagag aaatggattc agtataagga taaggaggga aggtggacca gaatgaaaac   3060
tgtaaatatt ttttaacct aatatcactt aaatcgaggc agaaagatat agacattcaa   3120
tgaattatat tcaatgcatt taaaatacca ctgtaattga cagagtaaaa gtatagatac   3180
aaaaccttgt gtaagaggct gacttttcca aataaacatt ttttaagaaa acatttcttc   3240
tcccaaatgt ctattttctt gaggaaaata ttgctgtgtc ttcattttca ttaccaggtt   3300
tcattttggg ccttgctaaa ttgattgaat taaatcctcc agcttttgaa ccttgaaaaa   3360
aaaaaaaaaa aaaaaaaaaa aaaaaaaaaa agaaaaaaaa aaaaaaaaag             3410
```

<210> SEQ ID NO 2
<211> LENGTH: 26
<212> TYPE: DNA
<213> ORGANISM: Artificial
<220> FEATURE:
<223> OTHER INFORMATION: MCT1 forward primer

<400> SEQUENCE: 2
tgccactgaa ttgatacctt tgctcc                                          26

<210> SEQ ID NO 3
<211> LENGTH: 26
<212> TYPE: DNA
<213> ORGANISM: Artificial
<220> FEATURE:
<223> OTHER INFORMATION: MCT1 reverse primer

<400> SEQUENCE: 3
tgctcatggc cctgggtcaa tcctaa                                          26

<210> SEQ ID NO 4
<211> LENGTH: 26
<212> TYPE: DNA
<213> ORGANISM: Artificial
<220> FEATURE:
<223> OTHER INFORMATION: MCT2 forward primer

<400> SEQUENCE: 4
gcaacaaaag atcgcaaaca gtaacg                                          26

<210> SEQ ID NO 5
<211> LENGTH: 26
<212> TYPE: DNA
<213> ORGANISM: Artificial
<220> FEATURE:
<223> OTHER INFORMATION: MCT2 reverse primer

<400> SEQUENCE: 5
tccgacgaaa aatgaacctt gaagag                                          26

<210> SEQ ID NO 6
<211> LENGTH: 26
<212> TYPE: DNA
<213> ORGANISM: Artificial
<220> FEATURE:
<223> OTHER INFORMATION: MCT3 forward primer

<400> SEQUENCE: 6
agccccacag ttaccagccg cctata                                          26

<210> SEQ ID NO 7
<211> LENGTH: 26
<212> TYPE: DNA
<213> ORGANISM: Artificial
<220> FEATURE:
<223> OTHER INFORMATION: MCT reverse primer

<400> SEQUENCE: 7
ggctgaagtt gggggtagga tggtgg                                          26

<210> SEQ ID NO 8
<211> LENGTH: 26
<212> TYPE: DNA
<213> ORGANISM: Artificial
<220> FEATURE:
<223> OTHER INFORMATION: MCT4 forward primer

<400> SEQUENCE: 8
aagccccaca gttaccagcc gcctat                                          26

<210> SEQ ID NO 9
<211> LENGTH: 26
<212> TYPE: DNA
<213> ORGANISM: Artificial

```
<220> FEATURE:
<223> OTHER INFORMATION: MCT4 reverse primer

<400> SEQUENCE: 9
tggcaatata ggagactggg gctgaa                                              26

<210> SEQ ID NO 10
<211> LENGTH: 26
<212> TYPE: DNA
<213> ORGANISM: Artificial
<220> FEATURE:
<223> OTHER INFORMATION: MCT5 forward primer

<400> SEQUENCE: 10
tgctgggatg gctgttcttt ctggac                                              26

<210> SEQ ID NO 11
<211> LENGTH: 26
<212> TYPE: DNA
<213> ORGANISM: Artificial
<220> FEATURE:
<223> OTHER INFORMATION: MCT5 reverse primer

<400> SEQUENCE: 11
tgccagagaa atagaaagag cccacg                                              26

<210> SEQ ID NO 12
<211> LENGTH: 26
<212> TYPE: DNA
<213> ORGANISM: Artificial
<220> FEATURE:
<223> OTHER INFORMATION: MCT6 forward primer

<400> SEQUENCE: 12
ctttggccct aggacagaca cacttc                                              26

<210> SEQ ID NO 13
<211> LENGTH: 26
<212> TYPE: DNA
<213> ORGANISM: Artificial
<220> FEATURE:
<223> OTHER INFORMATION: MCT6 reverse primer

<400> SEQUENCE: 13
actcgctcat ccacctcttc cttacg                                              26

<210> SEQ ID NO 14
<211> LENGTH: 26
<212> TYPE: DNA
<213> ORGANISM: Artificial
<220> FEATURE:
<223> OTHER INFORMATION: MCT7 forward primer

<400> SEQUENCE: 14
attcgaaggt gtggtctagt ggttgg                                              26

<210> SEQ ID NO 15
<211> LENGTH: 26
<212> TYPE: DNA
<213> ORGANISM: Artificial
<220> FEATURE:
<223> OTHER INFORMATION: MCT7 reverse primer

<400> SEQUENCE: 15
ggaaatggat cttgggaaat gtgagc                                              26
```

```
<210> SEQ ID NO 16
<211> LENGTH: 26
<212> TYPE: DNA
<213> ORGANISM: Artificial
<220> FEATURE:
<223> OTHER INFORMATION: MCT8 forward primer

<400> SEQUENCE: 16
gccgccttct tgttgtctat cgtggg                                            26

<210> SEQ ID NO 17
<211> LENGTH: 26
<212> TYPE: DNA
<213> ORGANISM: Artificial
<220> FEATURE:
<223> OTHER INFORMATION: MCT8 reverse primer

<400> SEQUENCE: 17
ggccaggctg aagagatagg ggacgt                                            26

<210> SEQ ID NO 18
<211> LENGTH: 26
<212> TYPE: DNA
<213> ORGANISM: Artificial
<220> FEATURE:
<223> OTHER INFORMATION: MCT9 forward primer

<400> SEQUENCE: 18
aaggcgatgt cataggtctg ggtcca                                            26

<210> SEQ ID NO 19
<211> LENGTH: 26
<212> TYPE: DNA
<213> ORGANISM: Artificial
<220> FEATURE:
<223> OTHER INFORMATION: MCT9 reverse primer

<400> SEQUENCE: 19
cttcccgtat gtgaccacga agactg                                            26

<210> SEQ ID NO 20
<211> LENGTH: 26
<212> TYPE: DNA
<213> ORGANISM: Artificial
<220> FEATURE:
<223> OTHER INFORMATION: MCT10 forward primer

<400> SEQUENCE: 20 aggggggcttt tatcaatgtg tgctcc                                           26

<210> SEQ ID NO 21
<211> LENGTH: 26
<212> TYPE: DNA
<213> ORGANISM: Artificial
<220> FEATURE:
<223> OTHER INFORMATION: MCT10 reverse primer

<400> SEQUENCE: 21
ccccagaacc agaggaggag gcagtg                                            26

<210> SEQ ID NO 22
<211> LENGTH: 26
<212> TYPE: DNA
<213> ORGANISM: Artificial
<220> FEATURE:
<223> OTHER INFORMATION: MCT11 forward primer
```

<400> SEQUENCE: 22
tcccgtaggc agcaatcagg tgtttc                                    26

<210> SEQ ID NO 23
<211> LENGTH: 26
<212> TYPE: DNA
<213> ORGANISM: Artificial
<220> FEATURE:
<223> OTHER INFORMATION: MCT11 reverse primer

<400> SEQUENCE: 23
gtggggtgtt tctggcgact ggagta                                    26

<210> SEQ ID NO 24
<211> LENGTH: 26
<212> TYPE: DNA
<213> ORGANISM: Artificial
<220> FEATURE:
<223> OTHER INFORMATION: Mouse MCT1 forward primer

<400> SEQUENCE: 24
aggggctctg aggtgttggt tcttag                                    26

<210> SEQ ID NO 25
<211> LENGTH: 26
<212> TYPE: DNA
<213> ORGANISM: Artificial
<220> FEATURE:
<223> OTHER INFORMATION: Mouse MCT1 reverse primer

<400> SEQUENCE: 25
caaaagcaca tccattcagt cggtac                                    26

<210> SEQ ID NO 26
<211> LENGTH: 26
<212> TYPE: DNA
<213> ORGANISM: Artificial
<220> FEATURE:
<223> OTHER INFORMATION: Human MCT1 forward primer

<400> SEQUENCE: 26
tgggcatgtg gcgtcgtcct aattat                                    26

<210> SEQ ID NO 27
<211> LENGTH: 26
<212> TYPE: DNA
<213> ORGANISM: Artificial
<220> FEATURE:
<223> OTHER INFORMATION: Human MCT1 reverse primer

<400> SEQUENCE: 27
ttcctcctcc ttgggccctc cttctg                                    26

<210> SEQ ID NO 28
<211> LENGTH: 26
<212> TYPE: DNA
<213> ORGANISM: Artificial
<220> FEATURE:
<223> OTHER INFORMATION: Human GLUT1 forward primer

<400> SEQUENCE: 28
ggggcatgat tggctccttc tctgtg                                    26

<210> SEQ ID NO 29

```
<211> LENGTH: 26
<212> TYPE: DNA
<213> ORGANISM: Artificial
<220> FEATURE:
<223> OTHER INFORMATION: Human GLUT1 reverse primer

<400> SEQUENCE: 29
aggccgcagt acacaccgat gatgaa                                          26

<210> SEQ ID NO 30
<211> LENGTH: 26
<212> TYPE: DNA
<213> ORGANISM: Artificial
<220> FEATURE:
<223> OTHER INFORMATION: Mouse GLUT1 forward primer

<400> SEQUENCE: 30
cgcccattcc tgtctcttcc taccca                                          26

<210> SEQ ID NO 31
<211> LENGTH: 26
<212> TYPE: DNA
<213> ORGANISM: Artificial
<220> FEATURE:
<223> OTHER INFORMATION: Mouse GLUT1 reverse primer

<400> SEQUENCE: 31
tcatggtgtt tgtgtggccc tcagtg                                          26

<210> SEQ ID NO 32
<211> LENGTH: 26
<212> TYPE: DNA
<213> ORGANISM: Artificial
<220> FEATURE:
<223> OTHER INFORMATION: Rat GLUT1 forward primer

<400> SEQUENCE: 32
gaaccacagg gaaagcaact ctaatc                                          26

<210> SEQ ID NO 33
<211> LENGTH: 26
<212> TYPE: DNA
<213> ORGANISM: Artificial
<220> FEATURE:
<223> OTHER INFORMATION: Rat GLUT1 reverse primer

<400> SEQUENCE: 33
tcgggtcatt atttttcacg tttcca                                          26

<210> SEQ ID NO 34
<211> LENGTH: 26
<212> TYPE: DNA
<213> ORGANISM: Artificial
<220> FEATURE:
<223> OTHER INFORMATION: Human BNP1 forward primer

<400> SEQUENCE: 34 cacccccgc tttcctttat ctccag                                           26

<210> SEQ ID NO 35
<211> LENGTH: 26
<212> TYPE: DNA
<213> ORGANISM: Artificial
<220> FEATURE:
<223> OTHER INFORMATION: Human BNP1 reverse primer

<400> SEQUENCE: 35
```
ctgctggtag gggagatgtg aagtgg                                          26

<210> SEQ ID NO 36
<211> LENGTH: 26
<212> TYPE: DNA
<213> ORGANISM: Artificial
<220> FEATURE:
<223> OTHER INFORMATION: Mouse BNP1 forward primer

<400> SEQUENCE: 36
acgggggaca tcactcagaa ttacat                                         26

<210> SEQ ID NO 37
<211> LENGTH: 26
<212> TYPE: DNA
<213> ORGANISM: Artificial
<220> FEATURE:
<223> OTHER INFORMATION: Mouse BNP1 reverse primer

<400> SEQUENCE: 37
ttcttccttt ttctcccagc cgttag                                         26

<210> SEQ ID NO 38
<211> LENGTH: 26
<212> TYPE: DNA
<213> ORGANISM: Artificial
<220> FEATURE:
<223> OTHER INFORMATION: Rat BNP1 forward primer

<400> SEQUENCE: 38
gccacacaca gcacagttca gcctcc                                         26

<210> SEQ ID NO 39
<211> LENGTH: 26
<212> TYPE: DNA
<213> ORGANISM: Artificial
<220> FEATURE:
<223> OTHER INFORMATION: Rat BNP1 reverse primer

<400> SEQUENCE: 39
ggacagcact gggcacaagg gaagac                                         26

<210> SEQ ID NO 40
<211> LENGTH: 26
<212> TYPE: DNA
<213> ORGANISM: Artificial
<220> FEATURE:
<223> OTHER INFORMATION: Mouse GFAP forward primer

<400> SEQUENCE: 40
aggaaattgc tggagggcga agaaaa                                         26

<210> SEQ ID NO 41
<211> LENGTH: 26
<212> TYPE: DNA
<213> ORGANISM: Artificial
<220> FEATURE:
<223> OTHER INFORMATION: Mouse GFAP reverse primer

<400> SEQUENCE: 41
caccatcccg catctccaca gtcttt                                         26

<210> SEQ ID NO 42
<211> LENGTH: 26
<212> TYPE: DNA

```
<213> ORGANISM: Artificial
<220> FEATURE:
<223> OTHER INFORMATION: Rat GFAP forward primer

<400> SEQUENCE: 42
ggtgggcagg tgaggaagaa atggag                                          26

<210> SEQ ID NO 43
<211> LENGTH: 26
<212> TYPE: DNA
<213> ORGANISM: Artificial
<220> FEATURE:
<223> OTHER INFORMATION: Rat GFAP reverse primer

<400> SEQUENCE: 43
tagcagaggt gacaaggggg ggagtg                                          26

<210> SEQ ID NO 44
<211> LENGTH: 2355
<212> TYPE: DNA
<213> ORGANISM: Artificial
<220> FEATURE:
<223> OTHER INFORMATION: hMCT1-rCD147 fusion protein

<400> SEQUENCE: 44
atggcggcgg cgctgctgct ggcgctggcc ttcacgttcc tgagtggcca aggcgcctgc      60
gcggcggcgg gcaccatcgt aacctctgtc caggaagttg actccaagac acagcttacc     120 tgcttttttga acagcagtgg cattgacatc gttggccacc gctggatgag aggtggcaag     180
gtactgcagg aagacacgct gcccgatcta cagatgaagt acacggtgga tgcagatgac     240
cgctctggag aatattcctg catcttcctt cctgagcctg tgggcagagg caacatcaat     300
gtggaggggc cacccaggat caaggtggga agaaatcgg aacacgccag tgagggagag     360
tttgtgaagc tgatctgcaa gtctgaggcg tcccaccctc ctgtggatga gtgggtctgg     420
tttaagacct ctgacactgg ggaccagact atctccaacg gcactgaggc caatagcaag     480
tacgtcatta tatccacgcc tgagctgtca gagctgatca tcagcgacct ggacatgaac     540
gtggaccctg gcacctacgt gtgcaatgcc accaactccc agggcagtgc tcgggagacc     600
atctcactgc gtgtgcgcag ccgcctggca gccctctggc ccttcctggg cattgtggcc     660
gaggtcctgg tgttggtcac catcatcttc atctacgaga gaggcggaa gccggaccag     720 accctggacg aggatgatcc tggcgccgcc ccactgaagg gcagcgggtc tcacctgaat     780
gacaaggaca gaatgtgcg ccagaggaac gccaccggag caggagcagg agcaggagca     840
gggagcgcta aaatgccacc agcagttgga ggtccagttg gatacacccc cccagatgga     900 ggctgggggct gggcagtggt aattggagct tcatttccca tcggcttctc ttatgcattt     960
cccaaatcaa ttactgtctt cttcaaagag attgaaggta tattccatgc caccaccagc    1020
gaagtgtcat ggatatcctc cataatgttg gctgtcatgt atggtggagg tcctatcagc    1080
agtatcctgg tgaataaata tggaagtcgt atagtcatga ttgttggtgg ctgcttgtca    1140
ggctgtggct tgattgcagc ttcttttctgt aacaccgtac agcaactata cgtctgtatt    1200
ggagtcattg gaggtcttgg gcttgccttc aacttgaatc agctctgac catgattggc    1260 aagtatttct acaagaggcg accattgcc aacggactgg ccatgcagg cagccctgtg    1320 ttcctctgta ctctggcccc cctcaatcag gttttcttcg gtatctttgg atggagagga    1380
agctttctaa ttcttggggg cttgctacta aactgctgtg ttgctggagc cctcatgcga    1440
ccaatcgggc ccaagccaac caaggcaggg aaagataagt ctaaagcatc ccttgagaaa    1500
```

```
gctggaaaat ctggtgtgaa aaaagatctg catgatgcaa atacagatct tattggaaga    1560
caccctaaac aagagaaacg atcagtcttc caaacaatta atcagttcct ggacttaacc    1620
ctattcaccc acagaggctt tttgctatac ctctctggaa atgtgatcat gttttttgga    1680
ctctttgcac ctttggtgtt tcttagtagt tatgggaaga gtcagcatta ttctagtgag    1740
aagtctgcct tccttctttc cattctggct tttgttgaca tggtagcccg accatctatg    1800
ggacttgtag ccaacacaaa gccaataaga cctcgaattc agtatttctt tgcggcttcc    1860
gttgttgcaa atgagtgtg tcatatgcta gcacctttat ccactaccta tgttggattc    1920
tgtgtctatg cgggattctt tggatttgcc ttcgggtggc tcagctccgt attgtttgaa    1980
acattgatgg accttgttgg accccagagg ttctccagcg ctgtgggatt ggtgaccatt    2040
gtggaatgct gtcctgtcct cctggggcca ccacttttag gtcggctcaa tgacatgtat    2100
ggagactaca atacacata ctgggcatgt ggcgtcgtcc taattatttc aggtatctat    2160
ctcttcattg gcatgggcat caattatcga cttttggcaa agaacagaa agcaaacgag    2220 cagaaaaagg aaagtaaaga ggaagagacc agtatagatg ttgctgggaa gccaaatgaa    2280
gttaccaaag cagcagaatc tccggaccag aaagacacag aaggagggcc caaggaggag    2340
gaaagtccag tctga                                                     2355
```

<210> SEQ ID NO 45
<211> LENGTH: 784
<212> TYPE: PRT
<213> ORGANISM: Artificial
<220> FEATURE:
<223> OTHER INFORMATION: hMCT1-rCD147 fusion protein

<400> SEQUENCE: 45

```
Met Ala Ala Leu Leu Ala Leu Ala Phe Thr Phe Leu Ser Gly
1               5                   10                  15

Gln Gly Ala Cys Ala Ala Ala Gly Thr Ile Val Thr Ser Val Gln Glu
                20                  25                  30

Val Asp Ser Lys Thr Gln Leu Thr Cys Phe Leu Asn Ser Ser Gly Ile
            35                  40                  45

Asp Ile Val Gly His Arg Trp Met Arg Gly Lys Val Leu Gln Glu
        50                  55                  60

Asp Thr Leu Pro Asp Leu Gln Met Lys Tyr Thr Val Asp Ala Asp Asp
65                  70                  75                  80

Arg Ser Gly Glu Tyr Ser Cys Ile Phe Leu Pro Glu Pro Val Gly Arg
                85                  90                  95

Gly Asn Ile Asn Val Glu Gly Pro Pro Arg Ile Lys Val Gly Lys Lys
            100                 105                 110

Ser Glu His Ala Ser Glu Gly Glu Phe Val Lys Leu Ile Cys Lys Ser
        115                 120                 125

Glu Ala Ser His Pro Pro Val Asp Glu Trp Val Trp Phe Lys Thr Ser
    130                 135                 140

Asp Thr Gly Asp Gln Thr Ile Ser Asn Gly Thr Glu Ala Asn Ser Lys
145                 150                 155                 160

Tyr Val Ile Ile Ser Thr Pro Glu Leu Ser Glu Leu Ile Ile Ser Asp
                165                 170                 175

Leu Asp Met Asn Val Asp Pro Gly Thr Tyr Val Cys Asn Ala Thr Asn
            180                 185                 190

Ser Gln Gly Ser Ala Arg Glu Thr Ile Ser Leu Arg Val Arg Ser Arg
        195                 200                 205
```

-continued

```
Leu Ala Ala Leu Trp Pro Phe Leu Gly Ile Val Ala Glu Val Leu Val
    210                 215                 220
Leu Val Thr Ile Ile Phe Ile Tyr Glu Lys Arg Arg Lys Pro Asp Gln
225                 230                 235                 240
Thr Leu Asp Glu Asp Pro Gly Ala Ala Pro Leu Lys Gly Ser Gly
                245                 250                 255
Ser His Leu Asn Asp Lys Asp Lys Asn Val Arg Gln Arg Asn Ala Thr
                260                 265                 270
Gly Ala Gly Ala Gly Ala Gly Ala Gly Ser Ala Lys Met Pro Pro Ala
            275                 280                 285
Val Gly Gly Pro Val Gly Tyr Thr Pro Asp Gly Gly Trp Gly Trp
        290                 295                 300
Ala Val Val Ile Gly Ala Phe Ile Ser Ile Gly Phe Ser Tyr Ala Phe
305                 310                 315                 320
Pro Lys Ser Ile Thr Val Phe Phe Lys Glu Ile Glu Gly Ile Phe His
                325                 330                 335
Ala Thr Thr Ser Glu Val Ser Trp Ile Ser Ser Ile Met Leu Ala Val
                340                 345                 350
Met Tyr Gly Gly Gly Pro Ile Ser Ser Ile Leu Val Asn Lys Tyr Gly
            355                 360                 365
Ser Arg Ile Val Met Ile Val Gly Gly Cys Leu Ser Gly Cys Gly Leu
    370                 375                 380
Ile Ala Ala Ser Phe Cys Asn Thr Val Gln Gln Leu Tyr Val Cys Ile
385                 390                 395                 400
Gly Val Ile Gly Gly Leu Gly Leu Ala Phe Asn Leu Asn Pro Ala Leu
                405                 410                 415
Thr Met Ile Gly Lys Tyr Phe Tyr Lys Arg Arg Pro Leu Ala Asn Gly
                420                 425                 430
Leu Ala Met Ala Gly Ser Pro Val Phe Leu Cys Thr Leu Ala Pro Leu
            435                 440                 445
Asn Gln Val Phe Phe Gly Ile Phe Gly Trp Arg Gly Ser Phe Leu Ile
        450                 455                 460
Leu Gly Gly Leu Leu Leu Asn Cys Cys Val Ala Gly Ala Leu Met Arg
465                 470                 475                 480
Pro Ile Gly Pro Lys Pro Thr Lys Ala Gly Lys Asp Lys Ser Lys Ala
                485                 490                 495
Ser Leu Glu Lys Ala Gly Lys Ser Gly Val Lys Lys Asp Leu His Asp
                500                 505                 510
Ala Asn Thr Asp Leu Ile Gly Arg His Pro Lys Gln Glu Lys Arg Ser
            515                 520                 525
Val Phe Gln Thr Ile Asn Gln Phe Leu Asp Leu Thr Leu Phe Thr His
        530                 535                 540
Arg Gly Phe Leu Leu Tyr Leu Ser Gly Asn Val Ile Met Phe Phe Gly
545                 550                 555                 560
Leu Phe Ala Pro Leu Val Phe Leu Ser Ser Tyr Gly Lys Ser Gln His
                565                 570                 575
Tyr Ser Ser Glu Lys Ser Ala Phe Leu Leu Ser Ile Leu Ala Phe Val
                580                 585                 590
Asp Met Val Ala Arg Pro Ser Met Gly Leu Val Ala Asn Thr Lys Pro
            595                 600                 605
Ile Arg Pro Arg Ile Gln Tyr Phe Phe Ala Ala Ser Val Val Ala Asn
        610                 615                 620
```

```
Gly Val Cys His Met Leu Ala Pro Leu Ser Thr Thr Tyr Val Gly Phe
625                 630                 635                 640

Cys Val Tyr Ala Gly Phe Phe Gly Phe Ala Phe Gly Trp Leu Ser Ser
                645                 650                 655

Val Leu Phe Glu Thr Leu Met Asp Leu Val Gly Pro Gln Arg Phe Ser
            660                 665                 670

Ser Ala Val Gly Leu Val Thr Ile Val Glu Cys Cys Pro Val Leu Leu
            675                 680                 685

Gly Pro Pro Leu Leu Gly Arg Leu Asn Asp Met Tyr Gly Asp Tyr Lys
            690                 695                 700

Tyr Thr Tyr Trp Ala Cys Gly Val Val Leu Ile Ile Ser Gly Ile Tyr
705                 710                 715                 720

Leu Phe Ile Gly Met Gly Ile Asn Tyr Arg Leu Leu Ala Lys Glu Gln
                725                 730                 735

Lys Ala Asn Glu Gln Lys Lys Glu Ser Lys Glu Glu Thr Ser Ile
            740                 745                 750

Asp Val Ala Gly Lys Pro Asn Glu Val Thr Lys Ala Ala Glu Ser Pro
            755                 760                 765

Asp Gln Lys Asp Thr Glu Gly Gly Pro Lys Glu Glu Glu Ser Pro Val
    770                 775                 780

<210> SEQ ID NO 46
<211> LENGTH: 55
<212> TYPE: PRT
<213> ORGANISM: Artificial
<220> FEATURE:
<223> OTHER INFORMATION: 55 amino acid residue chain portion of MCT1
      transporter

<400> SEQUENCE: 46

Arg Leu Leu Ala Lys Glu Gln Lys Ala Asn Glu Gln Lys Lys Glu Ser
1               5                   10                  15

Lys Glu Glu Glu Thr Ser Ile Asp Val Ala Gly Lys Pro Asn Glu Val
            20                  25                  30

Thr Lys Thr Ala Glu Ser Pro Asp Gln Lys Asp Thr Glu Gly Gly Pro
        35                  40                  45

Lys Glu Glu Glu Ser Pro Val
    50              55
```